United States Patent
Baru et al.

(10) Patent No.: US 10,183,168 B2
(45) Date of Patent: Jan. 22, 2019

(54) SYSTEMS AND METHODS FOR AUTOMATED CHARGE BALANCING OF MULTIPLE ELECTRODES FOR UNINTERRUPTED THERAPY AND EVOKED RESPONSE SENSING

(71) Applicant: BIOTRONIK SE & Co. KG, Berlin (DE)

(72) Inventors: Marcelo Baru, Tualatin, OR (US); Ramprasad Vijayagopal, Sugar Land, TX (US)

(73) Assignee: BIOTRONIK SE & Co. KG (DE)

( * ) Notice: Subject to any disclaimer, the term of this patent is extended or adjusted under 35 U.S.C. 154(b) by 0 days.

(21) Appl. No.: 15/451,838

(22) Filed: Mar. 7, 2017

(65) Prior Publication Data

US 2017/0259065 A1    Sep. 14, 2017

Related U.S. Application Data

(60) Provisional application No. 62/306,093, filed on Mar. 10, 2016.

(51) Int. Cl.
*A61N 1/36* (2006.01)
*A61N 1/05* (2006.01)

(52) U.S. Cl.
CPC ....... *A61N 1/36153* (2013.01); *A61N 1/0551* (2013.01); *A61N 1/36125* (2013.01); *A61N 1/36139* (2013.01); *A61N 1/36178* (2013.01)

(58) Field of Classification Search
CPC ............ A61N 1/36139; A61N 1/36153; A61N 1/36125
See application file for complete search history.

(56) References Cited

U.S. PATENT DOCUMENTS 5,674,264 A * 10/1997 Carter ................ A61N 1/36036
607/57
6,301,505 B1 10/2001 Money
(Continued)

FOREIGN PATENT DOCUMENTS

WO WO 97/21324 A1 6/1997
WO WO 2014/134075 A1 9/2014
WO WO 2015/164418 A1 10/2015

OTHER PUBLICATIONS

Anh Tuan Do et al., "A current-mode stimulator circuit with two-step charge balancing background calibration", Circuits and Systems (ISCAS), 2013 IEEE International Symposium ON, IEEE, May 10, 2013, pp. 409-412.

(Continued)

*Primary Examiner* — William Levicky
(74) *Attorney, Agent, or Firm* — Craig A. Fieschko, Esq.; Dewitt Ross & Stevens S.C.

(57) ABSTRACT

Electrical stimulation of a target (e.g., nervous tissue) is performed, wherein balance phases are automatically determined, and at least one of the electrodes is indirectly monitored during therapy delivery. The stimulation system is further configured to generate correction currents when a voltage accumulated at associated double layer capacitances crosses pre-defined thresholds so as to reduce or cancel the accumulated voltages without therapy interruption. A finer automatic determination of balance phases permits minimizing the stimulus artifact for evoked response sensing. Closed-loop neurostimulation may be performed based on such evoked responses.

18 Claims, 14 Drawing Sheets

(56) References Cited

U.S. PATENT DOCUMENTS

| | | |
|---|---|---|
| 9,656,084 B2 | 5/2017 | McDonald et al. |
| 9,700,724 B2 | 6/2017 | Liu et al. |
| 2008/0015641 A1* | 1/2008 | Armstrong ......... A61N 1/36142 607/2 |
| 2011/0125217 A1 | 5/2011 | Carter et al. |
| 2015/0306399 A1* | 10/2015 | McDonald ......... A61N 1/36146 607/62 |
| 2016/0045743 A1 | 2/2016 | Liu et al. |

OTHER PUBLICATIONS

International Search Report, Appln. No. 17159833.7-1666, dated Jul. 19, 2017.

* cited by examiner

US 10,183,168 B2

SYSTEMS AND METHODS FOR AUTOMATED CHARGE BALANCING OF MULTIPLE ELECTRODES FOR UNINTERRUPTED THERAPY AND EVOKED RESPONSE SENSING

CROSS-REFERENCE TO RELATED APPLICATIONS

This application claims priority under 35 USC § 119(e) to U.S. Provisional Patent Application 62/306,093 filed 10 Mar. 2016, the entirety of which is incorporated by reference herein.

FIELD OF THE INVENTION

The invention relates to systems and methods for automatic determination of charge balancing during electrical stimulation of a target using a pulse generator having at least one stimulating electrode, at least one return electrode, and at least one forced return electrode when two or more return electrodes are utilized for therapy.

BACKGROUND OF THE INVENTION

Upcoming neurostimulation applications (e.g., implantable neurostimulators) are demanding pulse generator architectures that can deal with multiple electrodes which are active at the same time, inject large currents and support high pulsing rates, with reduced electrode areas (to improve selectivity) and without interruption of stimulation. These constraints require systems and methods that can utilize information about the charge injection process to transparently modify stimulation patterns in order to avoid excessive electrode potential excursions and deal with mismatches between stimulating and return currents (used for active charge balancing) in order to avoid runaway issues in the DC blocking capacitors in series with each electrode. Managing the charge injection process can also permit minimizing the stimulus artifact (SA), allowing robust sensing of evoked responses caused by electrical stimulation, and possibly enabling closed-loop neurostimulation applications.

In traditionally programmed charge-balanced stimulation, the charge injected by a pulse generator in a stimulation pulse is followed by a balancing pulse of equal and opposite charge. This methodology assumes only reversible chemical reactions occur during therapy delivery, which may not be the case. For unipolar cathodic stimulation, E. Hudak proposed in "Electrochemical Evaluation of Platinum and Diamond Electrodes for Neural Stimulation" (PhD Thesis, Dept. of Chemical Engineering, Case Western University, May 2011) that a large value resistor may be placed across the DC blocking capacitor in series with the stimulating electrode to bleed off a portion of the stimulation charge, forcing the balancing anodic phase to have less charge, in an attempt to compensate for irreversible chemical reactions that may occur during therapy.

However, DC blocking capacitors are an important safety feature in the design of pulse generators. They are primarily used to limit the charge per phase, to reduce DC leakage, and to prevent DC current from circulating through tissue under a fault condition, among other functions. Although various approaches have been proposed for their elimination (as their size is an impediment to implant minimization), they continue to be employed in pulse generators owing to the safety they provide. Thus, placing a resistor across a DC blocking capacitor as proposed by Hudak is in contrast to the main purposes of the blocking capacitor, and may therefore impact compliance with tight DC-leakage requirements (e.g., 100 nA maximum) of clinical implantable active devices. Moreover, the compensation proposed by Hudak is open loop, causing the shift in electrode potential to be either positive or negative with respect to the open circuit potential (OCP) depending on the amount of imbalance generated by the charge bleeding.

Further, U.S. Pat. No. 6,301,505 B1 describes an electrical tissue stimulating device which includes circuitry for monitoring the build-up of undesirable residual voltages between stimulating electrodes and reducing such voltages in the event the condition occurs.

US 2011/0125217 A1 also describes measuring any residual charge remaining in an electrode that may result from an imbalance in the applied stimulation. More particularly, US 2011/0125217 A1 describes measuring the voltage across a DC blocking capacitor in series with an electrode to provide an accurate representation of the integral of the charge flow to the electrode, and thereby provide a measure of the residual charge on the electrode contact.

US2008/0015641 A1 describes electrical stimulation via electrodes, wherein the presence of a residual charge at the electrodes is measured via a differential voltage measurement, and action is taken in case thresholds are crossed.

SUMMARY OF THE INVENTION

The invention, which is defined by the claims at the end of this document, is addressed to methods and systems allowing automated charge balancing in a safe manner, and which reduces energy consumption overhead associated with such balancing.

The methods and systems for automatic charge balancing during electrical stimulation of a target (e.g., nervous tissue) use a pulse generator (e.g., an implantable pulse generator) having at least one stimulating electrode (W, X); at least one return electrode (Y); and at least one forced return electrode (Z) when two or more return electrodes are used. The stimulating electrode(s) (W, X) and the return electrode (Y) are configured to deliver electrical stimulation therapy, wherein each electrode (W, X, Y, Z) is coupled via a DC-blocking capacitor ($C_i$) to a current source (S), a current sink (S'), or a voltage. Each electrode forms a capacitance ($C_{dli}$) when forming a double layer with adjacent target material. In a determination stage, programmed stimulation current pulses ($I_{Ni}$) and automatically-determined balancing current pulses ($I_{Pi}$) for the respective electrode (i=W, X, Y, Z) are established such that the difference between the circulating balancing current pulse ($I_{Pi}$) minus the respective stimulation current pulse ($I_{Ni}$) through the respective electrode "i" satisfy the following conditions: (1) for the stimulating electrode(s) (W, X), the difference equals an automatically determined positive value; (2) for the return electrode (Y) and the forced return electrode (Z), the difference is positive and less than or equal to the minimum among the difference values for the stimulating electrodes (W, X); and (3) for each electrode (i=W, X, Y, Z), both its associated DC-blocking capacitor ($C_i$) and the associated capacitance ($C_{dli}$) charge in the same direction, and in opposite directions for stimulating and returning electrodes.

In a stimulation stage following the determination stage, stimulation cycles are repeatedly applied via the stimulating electrode(s) (W, X) and at least one return electrode (Y), with the stimulation cycles including programmed stimulation current pulses followed by automatically-determined balancing current pulses, with an open circuit phase between each balancing current pulse and the next stimulation current pulse. In the open circuit phase, no current is imposed via the stimulating electrode(s) (W, X). In the stimulation stage, at least one of the electrodes (i=W, X, Y, Z) is monitored, and when an accumulated voltage ($\Delta V_{dli}$) at the double layer of the monitored electrode(s) crosses pre-defined thresholds ($-\Delta V_{AddOCP}$, $\Delta V_{SubOCP}$), correction currents ($I_{CORRstim}$, $I_{CORRRet}$) are generated that reduce or cancel the accumulated voltages ($\Delta V_{dli}$) (including all accumulated voltages that did not reach a threshold).

The methods and systems thus allow an uninterrupted multi-electrode, controlled charge-imbalanced stimulation that maintains safe voltages at each active electrode, while avoiding runaway in the DC blocking capacitors caused by mismatches in the current drivers.

Preferably, the current sources, sinks, or voltages are coupled to the respective (stimulating, return, or forced return) electrode "i" via a respective DC-blocking capacitor $C_i$. Thus, there is no DC path between the current sources, sinks, or voltages and the respective electrode connected thereto via the associated DC blocking capacitor $C_i$.

The crossing of the safety threshold ($-\Delta V_{AddOCP}$, $\Delta V_{SubOCP}$) by the accumulated double layer voltage ($\Delta V_{dli}$) in electrode "i" is preferably automatically detected during therapy delivery by comparing (after P stimulating stages) the voltage on the terminal of the DC-blocking capacitor $C_i$ opposite the electrode under consideration (i.e., either voltages $V^*_{MUXStim}$, $V^*_{MUXRet}$, or $V^*_{MUXFor}$, depending on whether electrode "i" is a stimulating, a return, or a forced electrode respectively) versus the difference between an internally-generated voltage reference (either voltage $V_{REFStim}$, $V_{REFRet}$, or $V_{REFFor}$ respectively depending on the electrode role) and the estimated accumulated voltage at the DC blocking capacitor $C_i$ (i.e. either voltage $P^* \Delta V_{CStim}|^{Per\ Pulse}$, $P^* \Delta V_{CFor}|^{Per\ Pulse}$, where the $\Delta V$s are determined during the determination stage).

Crossing of the thresholds ($-\Delta V_{AddOCP}$, $\Delta V_{SubOCP}$) by the accumulated double layer voltage ($\Delta V_{dli}$) is preferably automatically detected by comparing the voltage on the terminal of the DC-blocking capacitor ($C_i$) opposite the electrode versus the difference between an internally-generated voltage reference and an estimated accumulated voltage ($P\Delta V_{CStim}|^{Per\ Pulse}$, $P\Delta V_{CRet}|^{Per\ Pulse}$, or $P\Delta V_{CFor}|^{Per\ Pulse}$) at the DC blocking capacitor ($C_i$).

The automatic determination of balancing current pulses is preferably performed for different patient postures, and/or depending on the stimulation frequency.

Preferably, the current difference representing the (necessary) charge imbalance is a minis mal current difference that ensures that at each electrode, both its associated DC blocking capacitor and the associated double layer capacitance charge in the same direction, and in opposite directions for stimulating and return electrodes.

During the determination stage, parameters that measure the final programmed unbalance for each active electrode may be stored. The stimulating and return electrodes with the largest voltage drift, as well as the forced return electrode (if required), can be selected for (indirect) monitoring during the stimulation stage. Alternatively, all electrodes (stimulating, return, and forced return electrodes) may be (indirectly) monitored.

The current difference (i.e., the necessary charge imbalance) may be determined for different patient postures, and/or depending on the stimulation frequency (i.e., the frequency of the stimulation stages applied via the electrodes).

The automatic determination of the current difference preferably involves letting each stimulating electrode, and also preferably each return electrode but the forced one (which is forced to handle the current mismatches), stimulate against a (pseudo) reference electrode which forms a return electrode in the determination stage. Preferably, the reference electrode is formed by the pulse generator's casing.

Preferably, automatic determination of the balancing current pulses involves letting each electrode for delivering electrical stimulation therapy stimulate against a reference electrode. The reference electrode is preferably formed by the pulse generator's casing.

The aforementioned detection of threshold crossing(s) is preferably conducted by means of a respective comparator which triggers when the threshold is crossed such that the correction currents are injected, and move the accumulated charges in the opposite direction. These correction phases can either be performed by having a separate active phase during part of the open circuit phases, or by adjusting successive balance phases (i.e., balancing current pulses).

Electrical stimulation depolarizes fibers, generating propagating action potentials. Evoked compound action potentials (ECAPs) are the sum of electroneurographic (ENG) activity recorded from a number of nerve fibers when these are stimulated above threshold. ECAPs have long been used to non-invasively or acutely assess nerve conduction, spinal cord integrity, and cochlear implant fitting, among other applications.

ECAPs amplitudes are typically in the tens of microvolt range, and their traditional recording is plagued with inherent electrical and other interfering signals which are orders of magnitude larger. For example, the stimulus artifact (SA), i.e., the non-propagating voltage transient produced as a result of electrical stimulation, is coherent with the ECAP signature, and thus cannot be reduced by averaging. Its amplitude may not only saturate the ECAP recording front-end, but its effect may extend beyond the duration of the stimulus pulse when the ECAP signature is to be recorded. Interference by much larger electromyographic (EMG) activity of nearby muscles and heart activity (ECG) may also affect ECAP recording.

The invention optimizes biphasic electrical stimulation to return the post-stimulation electrode potentials close to their open circuit potentials (OCPs), allowing a reduction of the stimulus artifact (SA). In a preferred arrangement, ECAPs are measured using a tripolar or quasi-tripolar arrangement of three recording electrodes which minimizes the effect of interfering signals (remnant SA, EMG, and ECG). Thus, the automatic determination of balancing current pulses is performed such that the stimulus artifact (SA) of a biphasic pulse for evoked compound action potential (ECAP) sensing is minimized.

In a preferred quasi-tripolar arrangement, two outer recording electrodes are tied together and connected to a non-inverting input of a single front-end configured for recording ECAPs, whereas a center recording electrode situated between said two outer recording electrodes is connected to the inverting input of the front-end.

Alternatively, where a (true) tripolar arrangement is used, two recording front-ends are provided wherein each front-end includes an output, with the outputs being summed to form a common output. Two outer recording electrodes are each connected to a non-inverting input of an associated front-end, and the inverting inputs of the two front-ends are tied together and connected to a central recording electrode arranged between the outer recording electrodes. Further, a component configured to compensate for misbalances in the recording impedances may be included to minimize pickup of potential interfering signals (e.g., EMG, ECG). This component may adjust the gains of the two front-ends via control signals, by minimizing the energy of the difference between the outputs of the two front-ends.

The pulse generator preferably includes at least one lead, and preferably a second (e.g., percutaneous) lead. The leads may extend along each other from a proximal end of the respective lead (adjacent to the casing of the pulse generator) to a distal end of the respective lead (remote from the casing). The stimulating electrode(s) may be arranged on one of the leads and may be guarded by at least one return electrode. The recording electrodes are also arranged on one of the leads.

The ECAP recording electrodes and the stimulating electrode(s) are preferably distanced from each other, particularly so as to minimize the SA. As an example, the recording electrodes may be arranged adjacent distal lead ends and the stimulating electrode(s) may be closer to proximal lead ends. The distance between them is preferably the maximal distance possible for the pulse generator/electrode configuration under consideration.

Preferably, following a programmable post-stimulus blanking period (i.e., after a stimulation current pulse and a succeeding balancing current pulse), intermediate electrodes (i.e., electrodes arranged between the stimulating and recording electrodes) are connected to a voltage reference $V_{REF}$ (preferably one internally generated by the pulse generator) via at least one or several switches. This allows referencing the body to a common voltage suitable for the ECAP recording front-end operation. The blanking may be accomplished by disconnecting the electrodes from the reference voltage $V_{REF}$.

Changes in the relative position of the leads with respect to each other (where more than one lead is provided), or of two inter-lead electrodes with respect to each other, may be detected using post-stimulus latency value changes of two ECAPs. Since the pulse generator controls both the timing of the stimulation current pulse delivery and the sampling of ECAPs, it can stimulate at the first end of the first lead and record at the second end of a second lead, thus maximizing the distance between stimulating and recording electrodes.

A suitable threshold may be defined in an initial ECAP signature, and the latency to the threshold may be automatically calculated. The latency value directly corresponds to the physical distance between the stimulating and recording electrode sites, and may be stored in the pulse generator for future comparisons.

To detect a change in relative position, the pulse generator is configured to initiate a new ECAP. To determine the new ECAP latency, the output of the ECAP recording fronts end(s) is compared against the threshold defined using the initial ECAP. Since no subsequent ECAP measurements are required following the initial one, the power and memory required for the purpose of determining relative lead migration is minimized. If the initial and subsequent latency values are within some acceptable pre-defined deviation, it can automatically be assumed that the leads (or electrodes, e.g. stimulating and recording electrodes) have not migrated relative to each other, or that they have migrated an acceptably small amount. An unacceptable deviation may, for example, be defined as an abrupt or significant short-term change from the initial latency value.

Upon detection of an unacceptable latency deviation, the pulse generator can dynamically alter the stimulation via the electrodes or current steering settings (i.e., weights of the stimulation and return currents). Additionally or alternatively, the pulse generator may generate an output signal notifying a physician of the migration of leads.

BRIEF DESCRIPTION OF THE DRAWINGS

Further versions, features, and advantages of the invention are described below with reference to the accompanying drawings, wherein.

DETAILED DESCRIPTION OF EXEMPLARY VERSIONS OF THE INVENTION

Figure 1:
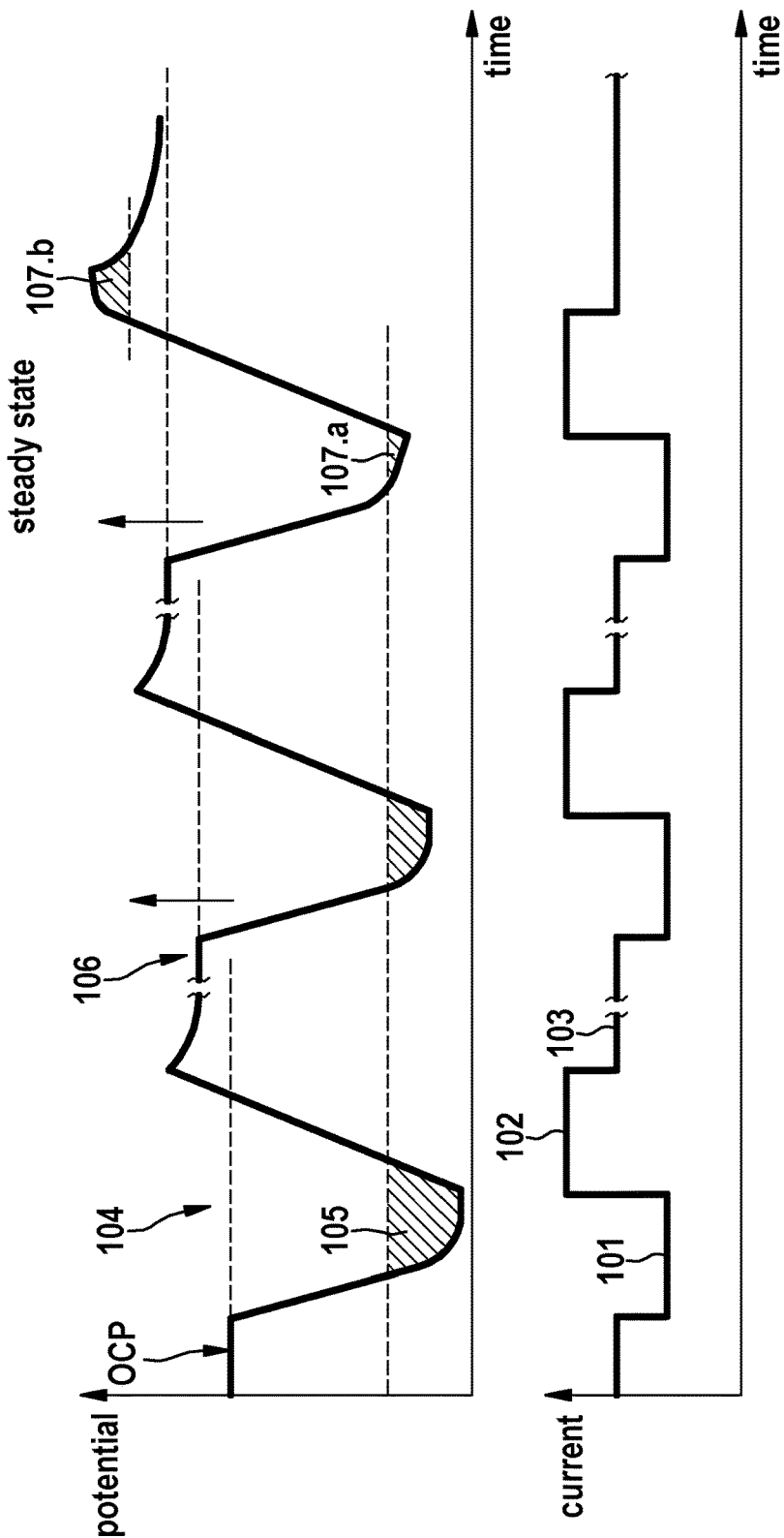
FIG. 1 shows an example of the potential of a stimulating electrode when an active charge-balanced stimulation protocol is used in a high rate pulsing application.

In the field of electrical stimulation, it is widely accepted that pulses having fully balanced charge are required for therapy delivery. FIG. 1 shows an example of the potential of a stimulating electrode when an active charge-balanced stimulation protocol is used in a high rate pulsing application. The stimulation pulse consists of a stimulation phase 101 (cathodic pulse) and a balance phase 102 (anodic pulse), followed by an open circuit phase 103 where no current is imposed by the pulse generator. The electrode potential begins from its open circuit potential (OCP), which is measured against a suitable voltage reference electrode. During delivery of the first cathodic pulse 104, the electrode-tissue double layer reversibly charges and the electrode may begin to transfer charge into Faradaic reactions 105 as its potential moves negatively. Since it is likely some irreversible charge transfer will occur during the stimulation phase 101, not all of the injected charge may go into charging the double layer. Hence, only a fraction of the cathodic charge of pulse 104 would be required during the anodic phase 102 to bring the potential back to OCP. If the anodic pulse 102 is balanced with the cathodic one 101 instead, as classically implemented in implantable pulse generators (IPGs), the pre-pulse potential 106 of successive pulses moves in the positive direction until the same amount of charge is lost during the cathodic and anodic phases shaded areas 107.a and 107.b. If this occurs, the anodic Faradaic reaction 107.b may cause electrode corrosion. In the case of a platinum (Pt) electrode, for example, Pt oxide (PtO) may be formed, and soluble Pt compounds—including toxic products such as cisplatin [$PtCl_2(NH_3)_2$]—may be generated when such PtO reacts in the chloride medium.

Figure 2:
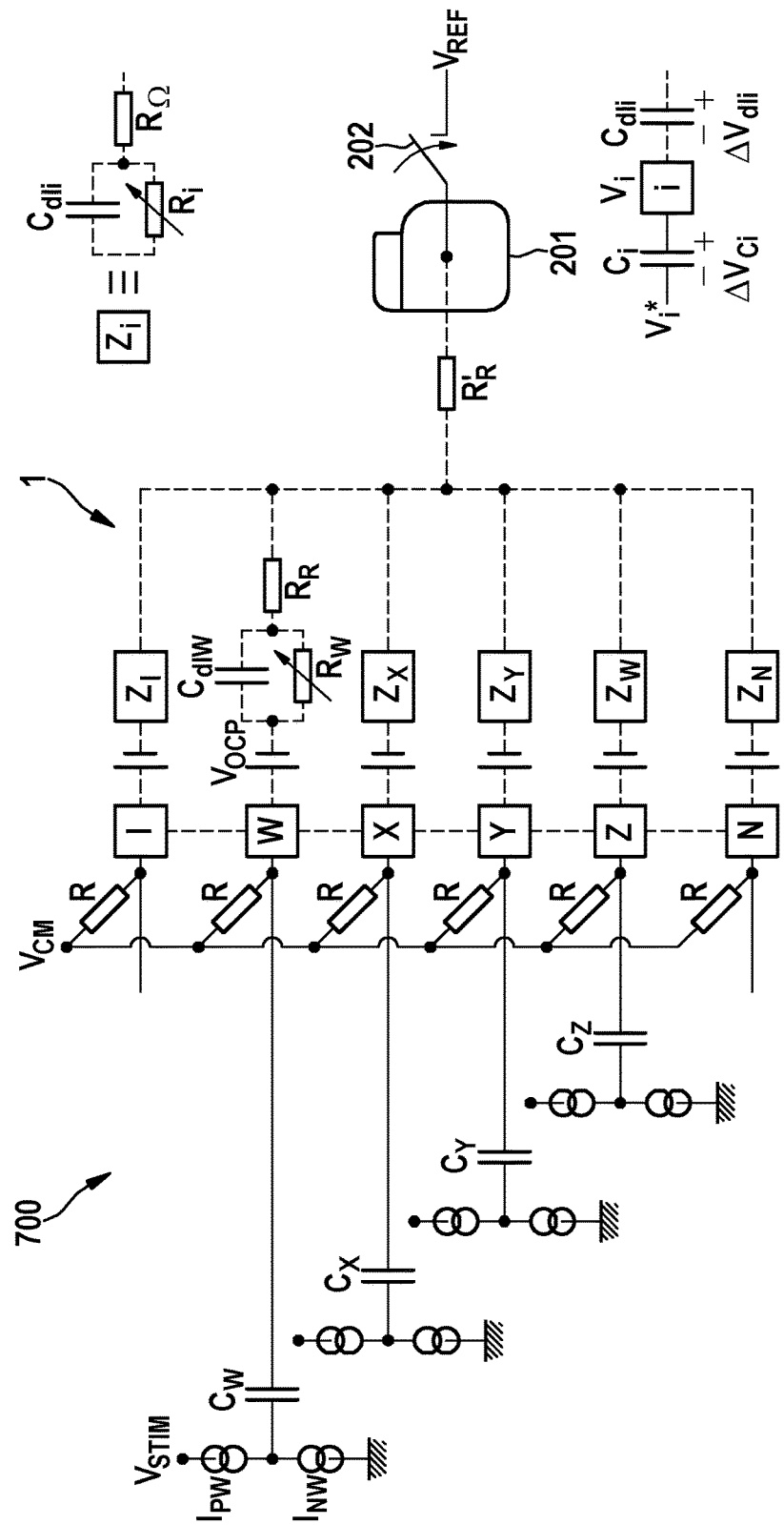
FIG. 2 schematically depicts an exemplary front-end of an implantable pulse generator in accordance with the invention.

FIG. 2 then illustrates an exemplary multi-electrode, multi-current front-end system 1 of a pulse generator in accordance with the invention. The pulse generator is preferably an IPG, but the invention also encompasses non-implantable pulse generators. The system 1 is configured to deliver stimulation with a scheme that automatically adjusts the injected charges to maintain safe operation, particularly to prevent voltage runaway in the DC blocking capacitors $C_i$ (where i denotes the electrode; blocking capacitors $C_W$, $C_X$, $C_Y$, $C_Z$ for electrodes i=W, X, Y, Z are shown, though more or fewer electrodes and blocking capacitors may be used).

During charge-imbalanced stimulation, the shift in pre-pulse potential may be either positive or negative with respect to the open circuit potential OCP depending on the amount of imbalance. Hence, to be able to monitor electrode voltage drift and compensate for it during therapy (without interruption, e.g., without the need to pause to drain charge), the system 1 delivers the minimum charge imbalance to ensure that at each active electrode, both its associated DC blocking capacitor $C_i$ and double layer (which are in series) charge in the same direction. The stimulating electrodes will charge in one direction, whereas the return electrodes will charge in the opposite direction to allow compensating when certain voltage limits are reached.

Determination of the necessary imbalance may be performed prior to therapeutic electrical stimulation of the target (e.g., tissue of a patient), for different patient postures, and depending on the stimulation frequency, by first independently cycling through each programmed stimulating electrode to be used for electrical stimulation, and stimulating (as programmed for electrical stimulation) against a pseudo reference electrode instead. Such pseudo reference may preferably be the IPG case 201. Thereafter, the system 1 cycles through all return electrodes except one, whereby this return electrode is forced to handle the current mismatches. During this "determination stage," parameters that measure the final programmed "unbalance" for each active electrode are saved, and the stimulation and return electrodes with the largest voltage drift, as well as the forced return electrode, are selected for indirect monitoring during the actual therapeutic electrical stimulation.

Once the determination stage is completed, electrical stimulation of the target is delivered as programmed. During the open circuit phases, the accumulated electrode-tissue double-layer voltages (of the electrodes selected for monitoring) are indirectly compared against variable reference voltages internally generated in the IPG 700. These comparators (exemplified by those in FIGS. 8 and 9) preferably allow monitoring the stimulation and return electrode voltages with the largest excursions, and the forced return electrode voltage, between programmable limits without directly accessing such electrode voltages. Unlike prior arrangements, there are no measurements during therapy (electrical stimulation of the target), only comparison of voltages that indirectly assess the double-layer voltages accumulated (e.g., a minimum of three voltages on the other side of the DC blocking capacitors for the selected electrodes). Advantageously, this approach reduces power consumption, as no amplifiers are used during the actual electrical stimulation of the target; minimizes time to decide on the status of the electrodes; and requires no DC path from an electrode.

Preferably, once a comparator triggers, correction phases take place to start moving the accumulated charges in the opposite direction. These correction phases can either be performed by having a separate active phase during part of the open circuit phases, or by adjusting successive balance phases.

Preferred arrangements for carrying out the invention will now be described in detail. FIG. 2 shows a schematic representation of a front-end of a classical multi-electrode (N electrodes) implantable pulse generator (IPG) 700, which may be configured as an IPG of a spinal cord stimulator (SCS), or as a neurostimulator designed for another application where current steering is desired, such as in nerve cuff stimulation of peripheral nerves. Each electrode-tissue interface is modelled by an impedance $Z_i$ (modelled at the top right of FIG. 2) composed of the parallel of the electrode-tissue double-layer capacitance $C_{dli}$ with a variable resistor $R_i$ (representative of Faradaic reactions that may occur during stimulation/balancing), in series with $R_\Omega$ (which represents the ohmic drop of the tissue electrolyte in the vicinity of an electrode).

Particularly, the IPG case 201 is made of a material that approximates a pseudo reference electrode (e.g. fractal Ir or TiN) and may have an effective area that makes its double-layer capacitance $C_{Case}$ (not shown) much larger than $C_{dli}$ (i=1 . . . N). The electrodes can be made, for example, of Pt, Pt/Ir, or fractal Ir. The open circuit potential (OCP) $V_{OCP}$ shown in FIG. 2 is against the IPG case 201 when the latter is connected to an internally-generated voltage reference $V_{REF}$ via switch 202. Since all electrodes are of the same material and have similar areas, it can be considered they all have the same $V_{OCP}$, as reflected in FIG. 2.

A similar $R'_\Omega$ represents the ohmic drop in the vicinity of the IPG case 201. The $R_\Omega$ and $R'_\Omega$ actual values are irrelevant, as voltage monitoring for safe operation occurs during the open circuit phases 103 when no current is imposed by the IPG 700 (or it can otherwise be neglected for the purpose of the analysis). The voltage $V_{STIM}$ in FIG. 2 is programmed with the required minimum overhead for steady-state stimulation.

$C_i$ represents the DC blocking capacitor associated with each electrode (i=1 . . . N, only $C_W$ to $C_Z$ shown in FIG. 2), which are nominally all equal. It can also be guaranteed by design that $C_{case}$ is much larger than $C_i$. Typically, the $C_i$ value used in IPGs is in the order of 10 µF. $C_{dli}$, on the other hand, can have a value on the order of (for example) 12.5 µF for an SCS Pt electrode. Fractal Ir coated electrodes will present a higher $C_{dli}$. In the case of nerve cuff electrodes, $C_{dli}$ may be lower. However, no particular relative values between $C_{dli}$ and $C_i$ are assumed for the purpose of implementing safe electrical stimulation.

Components R in FIG. 2 are bleeding resistors (preferably rated in the hundreds of kΩ), placed in star configuration, as typically utilized in IPG front-ends for passive charge neutrality. The invention preferably re-utilizes this network for the purpose of implementing safe stimulation, as described below. The IPG case 201 may also have a bleeding resistor connected to it, which would slightly alter the calculations shown below.

Figure 3:
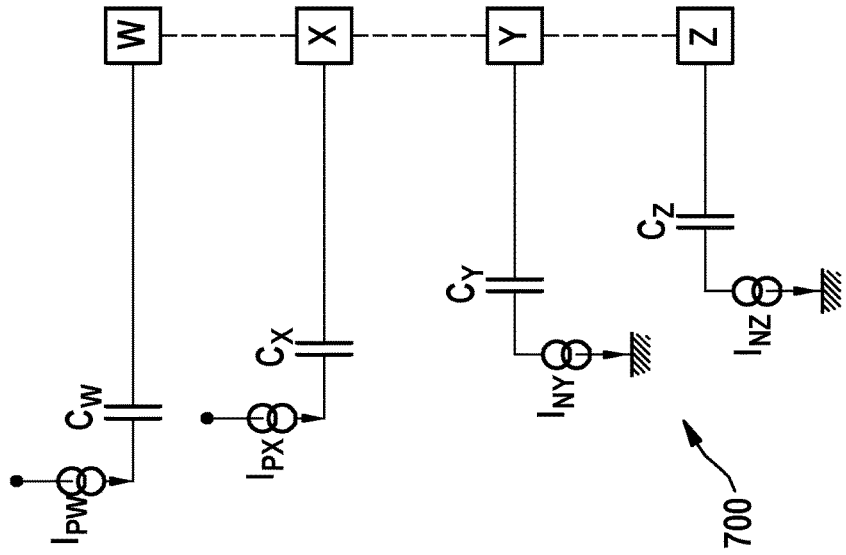
FIG. 3 shows an exemplary stimulation phase and balance phase of the pulse generator of FIG. 2.
Figure 3:
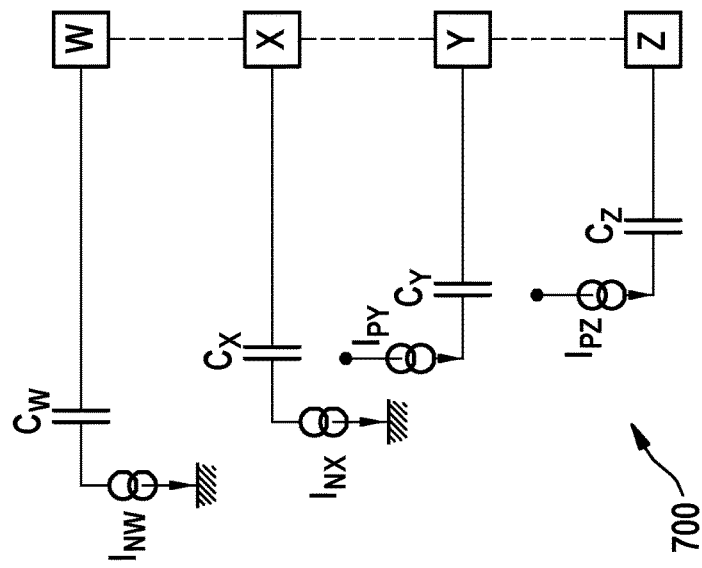

Assume that electrodes W, X, Y, Z are active during delivery of electrical stimulation to the target and that (for example) W, X are the stimulating electrodes and Y, Z the return electrodes of the stimulation phases, as shown in FIG. 3. During the stimulation phase, sinking currents $I_{NW}$ and $I_{NX}$ (will flow through electrodes W and X respectively, whereas sourcing currents $I_{PY}$ and $I_{PZ}$ flow through electrodes Y and Z. Currents are programmed so the total cathodic current equals the total anodic current, i.e. in this case $$I_{NW}+I_{NX}=I_{PY}+I_{PZ} \quad (1)$$

Assuming the sourcing currents (those from $V_{STIM}$) present larger output impedance than the sinking ones (those to ground or another voltage reference), the sinking currents will accommodate their real values to satisfy eq. (1). The system adjusts the output impedance of the current source associated with at least one of the return electrodes in the stimulation phase (e.g., contact Z) to implement tissue and electrode safe operation, as further described below.

An active balance phase has the reverse arrangement, as shown in FIG. 3, i.e., currents $I_{PW}$ and $I_{PX}$ flow instead through electrodes W and X respectively, whereas currents $I_{NY}$ and $I_{NZ}$ will flow through electrodes Y and Z.

For the actual electrical stimulation of the target (therapy), currents $I_{NW}$, $I_{NX}$, $I_{PY}$, and $I_{PZ}$, the stimulation phase pulse width ($PW_{Stim}$, common to all), the balance phase pulse width ($PW_{Bal}$, common to all), the interphase delay (i.e., the time between the end of a stimulation pulse and the start of the associated balancing pulse), and the stimulation frequency are typically selectable and programmable in an IPG 700. For high pulsing rates, and for closed-loop neurostimulation based on neural response, $PW_{Bal}$ is preferably selected equal to $PW_{Stim}$ and programmed as a single parameter pulse width (PW). The balance phase currents $I_{PW}$, $I_{PX}$, $I_{NY}$, and $I_{NZ}$ can be the unknowns the system may adjust to implement safe stimulation without therapy interruption, and to minimize the stimulation artifact (SA) for evoked response sensing. Thus, preferred versions of the invention automatically determine the balance phase currents for safe operation.

For safe tissue and electrode stimulation, the accumulated voltage of the equivalent double-layer capacitances ($\Delta V_{dli}$, where i=W, X, Y, Z in the example) should remain within a safe window. With the sign shown in FIG. 2 (bottom right), this translates into $$-\Delta V_{AddOCP} \leq \Delta V_{Vdli} \leq \Delta V_{SubOCP} \quad (2)$$

where $\Delta V_{SubOCP}$ and $\Delta V_{AddOCP}$ respectively limit the excursion of the electrode voltage in the negative and positive directions with respect to its open circuit potential (OCP). The limit values may be determined via in-vitro experiments using a suitable electrolyte, confirmed in-vivo, and programmed in the IPG 700. Preferably, the window is symmetrical and a few hundred mV wide (e.g. ±100 mV).

A preferred embodiment for safe stimulation is the following: prior to delivery of the actual electrical stimulation to the target and particularly for different patient postures, the IPG 700 first estimates $V_{OCP}$. To do so, it is configured to measure the common point $V_{CM}$ of the bleeding resistor network R (see FIG. 2), preferably via the circuit of FIG. 4 (switches 401 and 402 are closed) when the digital-to-analog converter block (DAC) outputs a reference voltage $V_{REF}$ and the IPG case 201 is connected to such voltage. In this case, the output put Vo of the amplifier AMP equals $$Vo=-NV_{OCP}+V_{REF} \quad (3)$$

which is preferably digitized via the analog-to-digital converter block (ADC). The $V_{OCP}$ is then calculated and stored in the IPG 700; N is typically 2, 4, 8, 16, or 32 in a neurostimulator, so digital division is straightforward. Switches 401 and 402 are particularly designed with negligible charge injection and on-resistance compared to R. The amplifier AMP offset is also negligible for the purpose of determining $V_{OCP}$. The resistor R in the feedback of amplifier AMP is preferably matched with the resistors R of FIG. 2 to reduce measurement error.

As previously mentioned, to be able to monitor voltage drift and compensate for it, the system 1 is preferably configured to deliver the minimum charge imbalance that guarantees (at each electrode) that both $C_i$ and $C_{dli}$ charge in the same direction. The stimulating electrodes (W and X in the example) and the return electrodes (Y and Z in the example) of the stimulation phase will charge in opposite directions to allow compensating once a limit given by condition (2) is reached.

Prior to the stimulation stage (where the actual electrical stimulation of the target takes place), the determination stage may proceed as follows. The system 1 preferably first cycles through each stimulating electrode independently (W and X in the example), and injects M (M=1, 2, 4, 8, . . . ) "balanced as-programmed pulses" (i.e. $I_{Pi}$ is automatically programmed by the IPG 700 equal to $I_{Ni}$) against the IPG case 201 (the return electrode in the determination stage). The balance will then only be limited by the current matching between the real $I_{Ni}$ and real $I_{Pi}$, which is typically calibrated for and a few percent apart. Parameter M may be selected to improve accuracy of the calculations detailed below. In between the cycling of electrodes W and X (in the example), a complete passive balance phase for electrode W and IPG case 201 (with hardware not shown in FIG. 2) is preferably performed to guarantee an electrical-neutral system before cycling the next electrode (X in the example). The same procedure applies when two or more stimulating electrodes are utilized instead for therapy.

For the determination stage, $V_{STIM}$ may be re-programmed with different values to mimic the actual varying voltage that will appear across each current source/sink during therapy. For electrode W, for example, $V_{STIM}$ may be temporarily re-programmed during the determination stage with a value equal to $$V_{DSn}+R_{W2casemax}*I_{NWmax}+(I_{NWmax}*PW)/C_{WdlWmin}$$

where $V_{DSn}$ is a "safe" compliance voltage required for the current sinks to operate, $R_{W2casemax}$ is the measured impedance between electrode W and the IPG case 201 increased by the measurement error, $I_{NWmax}$ is the stimulation current through electrode W increased by the allowable error, PW is the stimulation pulse width, and $C_{WdlWmin}$ is the measured series capacitor $C_W$, $C_{dlW}$ decreased by the measurement error. It is assumed that $V_{DSn}$ has enough overhead to accommodate the maximum steady-state accumulated voltage on $C_W$ and $C_{dlW}$ for the determination stage to properly operate under such reduced $V_{STIM}$. Given each electrode is much smaller than the IPG case 201, this setup emulates what each electrode will see under a multi-current therapy setup.

Figure 4:
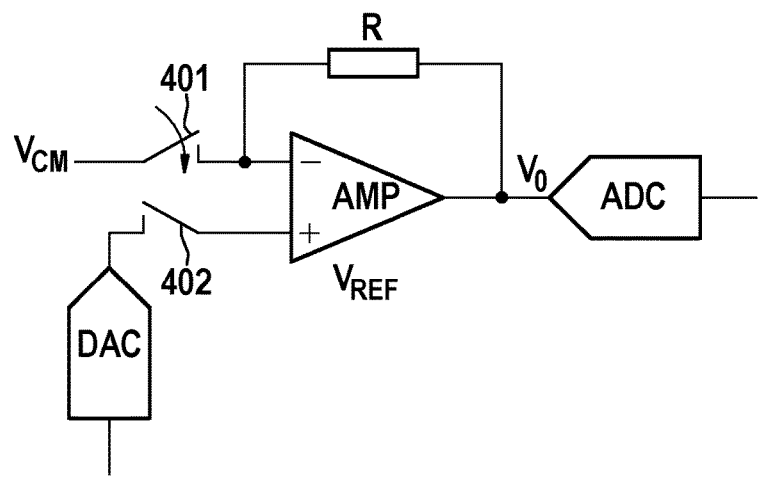
FIG. 4 shows an exemplary circuit for determining the open circuit potential (OCP).
Figure 5:
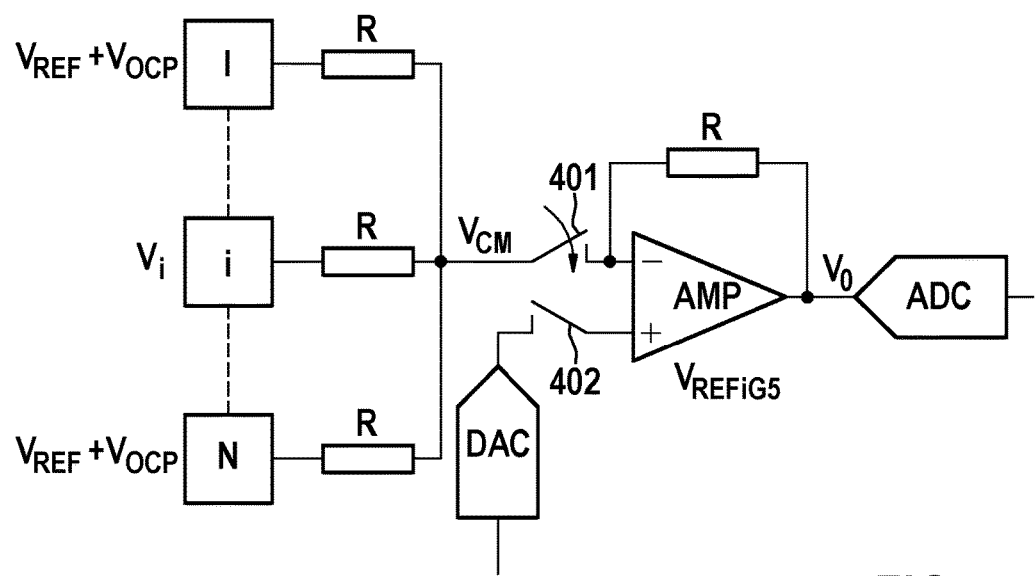
FIG. 5 shows the use of the circuit of FIG. 4 to measure accumulated voltage in a cycled electrode "i" during the determination stage.

After the M determination pulses in the stimulating electrode "i" (i=W or λ in the example), connecting again the circuit of FIG. 4 and the IPG case 201 results in the circuit of FIG. 5. All electrodes, except the cycled "i" (which was active), still present a voltage equal to ($V_{REF}+V_{OCP}$). Programming now the DAC block reference to a voltage $V_{REFFIG5}$ equal to such ($V_{REF}+V_{OCP}$) results in $$V_0 = \Delta V_{dli} + V_{REFFIG5} \quad (4)$$

$$V_i = -\Delta V_{dli} + V_{REF} + V_{OCP} = \Delta V_{dli} + V_{REFFIG5} \quad (5)$$

(see FIG. 2 for the defined sign of $\Delta V_{dli}$).

At the same time, the system 1 particularly also measures $V^*_i$, which is the voltage at the other terminal of the DC blocking capacitor $C_i$ of active electrode "i" cycled (see FIG. 2 bottom right). This is measured via the N to 3 multiplexer (MUX) block, switch 601 and buffer (AMP) shown in FIG. 6a ($V^*_{iBUF}$ is the output signal).

From $V_i$ determined above (see eq. (5)) and $V^*_{iBUF}$, the accumulated voltage $\Delta V_{Ci}$ (from current mismatches) on the blocking capacitor $C_i$ can be calculated as ($V_i - V^*_{iBUF}$) (see FIG. 2 for the sign of $\Delta V C_i$ as measured).

If both $\Delta V_{dli}$ and $\Delta V_{Ci}$ are positive, the balance phase for the cycled electrode "i" can be left as programmed for the determination stage. No adjustments are necessary as the positive voltages indicate the mismatch in the real $I_{Ni}$ and real $I_{Pi}$ is causing the balancing charge to be less than the stimulation charge. The misbalance current $I_{Diffi}$, i.e. real $I_{Ni}$-real $I_{Pi}$, can be estimated to be at least $$I_{Diffi} = [C_{imin}*(\Delta V_{Ci})]/(MPW)(i=W \text{ or } X \text{ in the example}) \quad (6)$$

where $C_{imin}$ is the minimum value of the DC blocking capacitor $C_i$, $\Delta V_{Ci}$ is the aforementioned measured accumulated voltage, and PW is the programmed pulse width as defined before.

On the other hand, if $\Delta V_{dli}$ is negative, this implies the electrode "i" potential would be moving positively pulse after pulse, so less balancing charge is required to avoid this situation. Preferably, the balancing charge reduction is determined as follows.

A prior impedance measurement allows estimating $C_{dli}$ for the electrode "i" under consideration (either W or X in the example), with a certain error. Thus, the current $I_{Lessi}$ to be subtracted from the automatically selected $I_{Pi}$ can be calculated as:

$$I_{Lessi} = [C_{dlimax}*(-\Delta V_{dli})](MPW) \; (i=W \text{ or } X \text{ or none in the example}) \quad (7)$$

where $C_{dlimax}$ is the measured $C_{dli}$ with the maximum added error, $\Delta V_{dli}$ is the accumulated double-layer voltage (see FIG. 2), and PW is the programmed pulse width as defined before.

A lookup table can be implemented in the IPG 700 to determine each $I_{Diffi}$, $I_{Lessi}$ based on the corresponding C, $\Delta V$, and (M PW).

For those electrodes with negative $\Delta V_{dli}$, $I_{Pi}$ will then be automatically re-programmed equal to $$\text{new } I_{Pi} = \text{old } I_{Pi} - I_{Lessi} \; (i=W \text{ or } X \text{ or none in the example}) \quad (8)$$

where $I_{Lessi}$ is the current estimated above.

Having a positive $\Delta V_{dli}$ and a negative $\Delta V_{Ci}$ is not possible, as the latter implies the automatically programmed $I_{Pi}$ was larger than the selected $I_{Ni}$ (by mismatch), which will always result in a negative $\Delta V_{dli}$ regardless of whether Faradaic reactions were present or not during the stimulation phase.

After initially cycling through all stimulating electrodes, a new set of M pulses, with the modified balance phase, is preferably injected for the stimulating electrodes that required $I_{Pi}$ adjustment. Their new $I_{Diffi}$ is then estimated and stored, and it is confirmed that both $C_i$ and $C_{dli}$ accumulated charge in the same direction.

At the end of this process, all stimulating electrodes "i" (W and X in the example) will in theory satisfy $$\text{real } I_{Pi} = \text{real } I_{Ni} - I_{Diffi} \quad (9)$$

The lowest value among the estimated $I_{Diffi}$ from all stimulating electrodes (W and X in the example) is stored in the IPG 700 as $I_{MinDiff}$. An alternative measure, such as the $\Sigma I_{Diffi}$ divided by the number of return electrodes in the stimulation phase, can instead be stored as $I_{MinDiff}$.

In this manner, $\Delta V_{Ci}$ for the stimulating electrodes (W and X in the example) will have the same positive sign as $\Delta V_{dli}$, as the real $I_{Pi}$ for therapy is guaranteed to be less than $I_{Ni}$.

However, $I_{Pi}$ was determined with only one electrode active. For the same $I_{Pi}$ to flow during therapy where all programmed electrodes are active simultaneously, at least a return electrode in the stimulation phase (e.g., Z, assuming that $I_{PZ}$ is the smallest return current amplitude of the stimulation phase) needs to be forced to present lower impedance than the sinking currents so that the $I_{Ni}$ currents get properly established.

On the other hand, in the case of the return electrodes of the stimulation phase, except for the one forced to have lower impedance (Z in the example), the balance phase currents are preferably automatically programmed equal to $$I_{Ni} = I_{Pi} - I_{MinDiff} \; (i=Y \text{ in the example}) \quad (10)$$

where $I_{MinDiff}$ was stored in the IPG 700 as described before.

The system 1 can then cycle independently through each return electrode of the stimulation phase except the forced one (only Y in the example), injecting again M (M=1, 2, 4, 8, . . . ) pulses with the selected $I_{Pi}$ and the automatically-programmed $I_{Ni}$ (see eq. (10)) against the IPG case 201a (the return electrode in this stage).

After the M pulses, the difference between the real $I_{Pi}$ and real $I_{Ni}$ can be estimated as follows $$(\text{real } I_{Pi} - \text{real } I_{Ni}) = [C_{imax}*(-\Delta V_{Ci})]/(MPW) \quad (11)$$

The system 1 then verifies $$0 < (\text{real } I_{Pi} - \text{real } I_{Ni}) \leq I_{MinDiff} \quad (12)$$

and (real $I_{Pi}$-real $I_{Ni}$) is defined as $\Delta I_i$.

If condition (12) is not satisfied, the system 1 can automatically adjust $I_{Ni}$ until condition (12) is satisfied, as $I_{Pi}$ is the programmable parameter of the stimulation phase.

The remaining sourcing/sinking currents of the stimulation/balance phase will circulate through the forced electrode (Z in the example).

In this way, the stimulating and return electrodes charge in opposite directions, allowing for compensation when one of the conditions (2) is reached.

Figure 7:
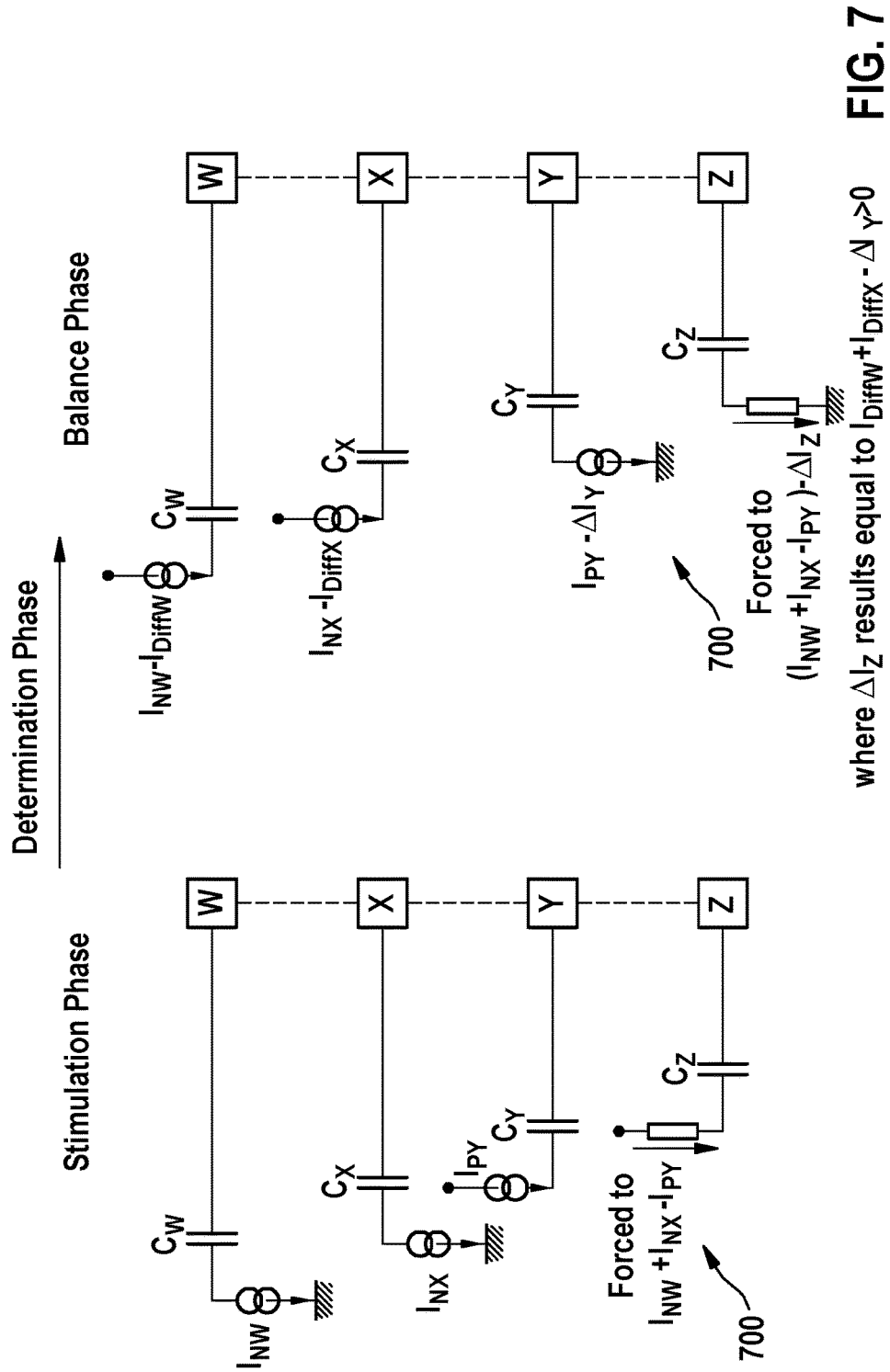
FIG. 7 shows a stimulation and balance phase following the determination stage described below.

To summarize, FIG. 7 shows the stimulation and balance phases (post determination stage) for the foregoing example. Programmable resistors, instead of a current source or sink, can be used to force electrode Z (which forms the forced return electrode in the example) to present lower impedance in both the stimulation and balance phases. Considering the stimulation phase, for example, such a resistor can be programmed equal to $$\{V_{SDp}/I_{pZmin}+[(I_{PYmax}/I_{PZmin})/C_{YdlYmin}-1/C_{ZdlZmax}]* \\ PW+[(I_{PYmax}/I_{PZmin})*R_{Y2allEmax}-R_{Z2allEmin}]\}$$

where $V_{SDp}$ is a "safe" compliance voltage required for the current sources to operate, min and max subscripts represent the respective parameters with added or subtracted errors, and $R_{i2allE}$ Y, Z in the example) is the impedance of electrode "i" against all other electrodes tied together. The selected resistance's appropriateness can be confirmed by compliance voltage monitoring across active sink and sourcing currents during the actual electrical stimulation of the target. If two or more return electrodes are programmed, electrode Z represents the electrode with the smallest programmed current.

As a final step of the determination stage, a new set of M pulses, with the determined balance phase, is preferably injected next for all active electrodes (i.e., both the stimulating and return electrodes), except for the forced one (Z in the example). The parameters $\Delta V_{dli}$ and $\Delta V_{Ci}|^{Per\ Pulse}$ for each electrode are now determined, the latter as the measured $\Delta V_{Ci}/M$ for the selected stimulating and return electrodes, and particularly as $$[(\Sigma I_{Diffi} - \Sigma \Delta I_i)*PW]/C_{imin}$$

for the forced electrode (Z in the example). These values are digitized and stored in the IPG 700. For the forced electrode (Z in the example), a new lookup table can be implemented to determine $\Delta V_{CFor}|^{Per\ Pulse}$ (the accumulated per-stimulation pulse voltage in the DC blocking capacitor associated with the forced electrode, Z in the example).

Figure 6A:
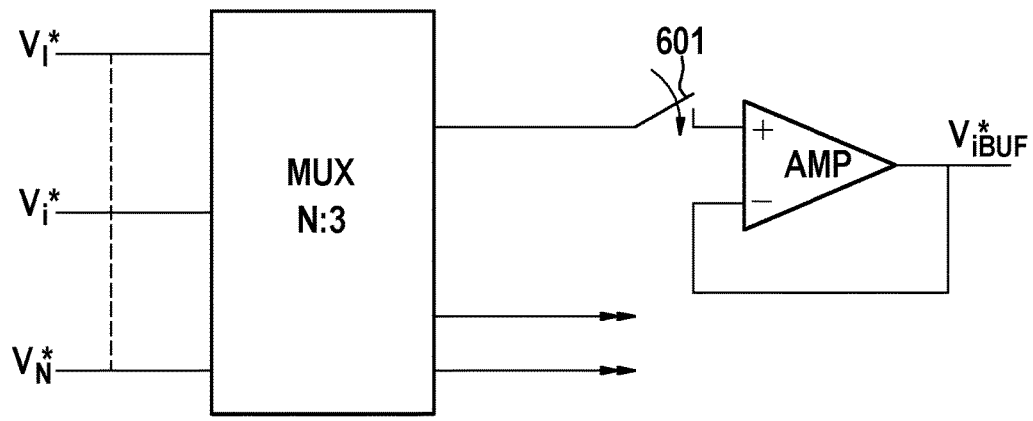
FIG. 6a shows an N to 3 multiplexer (MUX) block for measuring voltages.
Figure 6B:
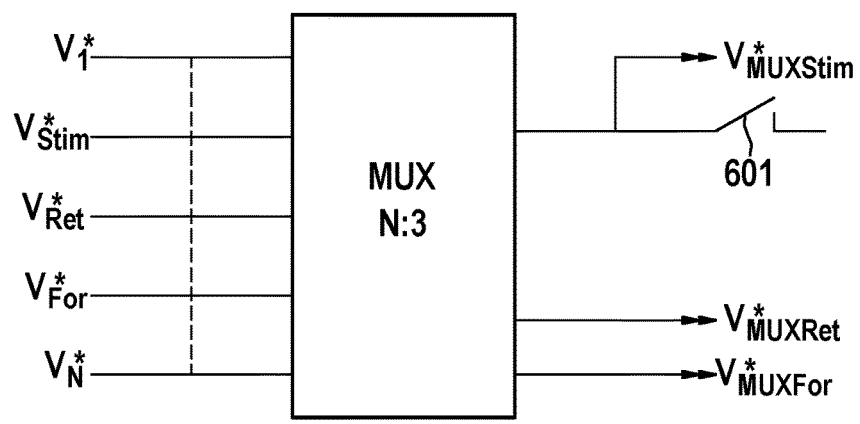
FIG. 6b shows the MUX block's use for monitoring electrodes.

The system 1 will preferably select and monitor (during delivery of the electrical stimulation to the target) the stimulating and return electrodes that presented the largest $|\Delta V_{dli}|$. It will also monitor the forced electrode (Z in the example). The voltages $V^*_{Stim}$, $V^*_{Ret}$, and $V^*_{For}$ (see FIG. 6b) of the selected stimulating, return, and forced electrodes will particularly be connected to $V^*_{MUXStim}$, $V^*_{MUXRet}$, and $V^*_{MUXFor}$ respectively via the MUX. The circuitry of FIG. 4/FIG. 5, except for the DAC, and the AMP of FIG. 6a are not needed for the actual electrical stimulation of the target so they may be turned off/disconnected to reduce power consumption.

In an alternative embodiment, all voltages of the participating active electrodes may be monitored instead.

As mentioned before, during electrical stimulation of the target, the system guarantees:

$$-\Delta V_{AddOCP} \leq \Delta V_{dli} \leq \Delta V_{SubOCP}\ (i=1\ldots N) \quad (13)\ (same\ as\ eq.\ (2))$$

Now, during an open circuit phase (where no current is imposed by the IPG 700), if the IPG case 201 is connected to $V_{REF}$, in particular one has for the monitored voltages:

$$V_{REF} + V_{OCP} - \Delta V_{dlOutput} - \Delta V_{COutput} - V^*_{MUXOutput} = 0 \quad (14)$$

(with the sign shown in FIG. 2) where Output is either Stim, Ret or For. Eq. (13) can be re-written as $$\Delta V_{dlOutput} = V_{REF} + V_{OCP} - \Delta V_{COutput} - V^*_{MUXOutput} \quad (15)$$

At the same time, after P stimulation pulses, $$\Delta V_{COutput} = \Sigma_{1\ to\ P} \Delta V_{COutput}|^{Per\ Pulse} = P * \Delta V_{COutput}|^{Per\ Pulse} \quad (16)$$

where the parameter $\Delta V_{COutput}|^{Per\ Pulse}$ was previously digitized and internally stored in the IPG 700 in the final step of the determination stage.

Hence from (13), (15) and (16), for the monitored voltages we have $$-\Delta V_{AddOCP} \leq V_{REF} + V_{OCP} - P * \Delta V_{COutput}|^{Per\ Pulse} - V^*_{MUXOutput} \leq \Delta V_{SubOCP} \quad (17)$$

Conditions (17) can be individually re-written as $$V^*_{MUXStim} \geq V_{REF} + V_{OCP} - \Delta V_{SubOCP} - P * \Delta V_{CStim}|^{Per\ Pulse} \quad (18.a)$$

$$V^*_{MUXRet} \leq V_{REF} + V_{OCP} + \Delta V_{AddOCP} - P * \Delta V_{CRet}|^{Per\ Pulse} \quad (18.b)$$

$$V^*_{MUXFor} \leq V_{REF} + V_{OCP} + \Delta V_{AddOCP} - P * \Delta V_{CFor}|^{Per\ Pulse} \quad (18.c)$$

It is worth noting that $\Delta V_{CRet}|^{Per\ Pulse}$ and $\Delta V_{CFor}|^{Per\ Pulse}$ in conditions 18.b and 18.c are negative so they add to the value on the right of the foregoing inequalities.

Conditions 18 can re-written as $$V^*_{MUXStim} \geq V_{REFStim} - P * \Delta V_{CStim}|^{Per\ Pulse} \quad (19.a)$$

$$V^*_{MUXRet} \leq V_{REFRet} - P * \Delta V_{CRet}|^{Per\ Pulse} \quad (19.b)$$

$$V^*_{MUXFor} \leq V_{REFRet} - P * \Delta V_{CFor}|^{Per\ Pulse} \quad (19.c)$$

where $V_{REFStim}$ and $V_{REFRet}$ are fixed voltages equal to $(V_{REF} + V_{OCP} - \Delta V_{SubOCP})$ and $(V_{REF} + V_{OCP} + \Delta V_{AddOCP})$ respectively.

Figure 8:
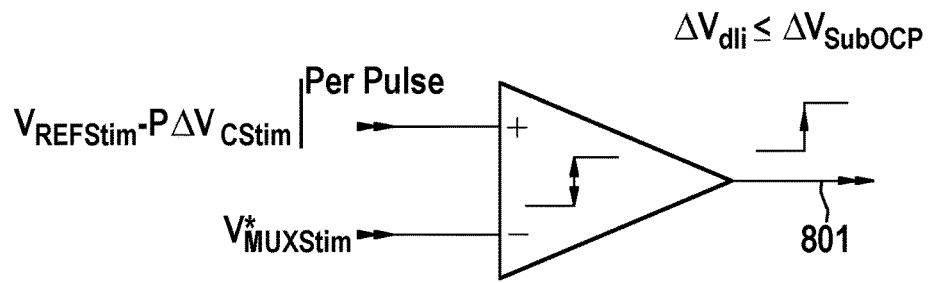
FIGS. 8 and 9 show comparators for indirectly monitoring the accumulated double layer voltages.

In a preferred version of the system 1, condition 19.a is implemented by the comparator of FIG. 8, where an extra DAC block generates a variable reference that subtracts the stored $\Delta V_{CStim}|^{Per\ Pulse}$ after each stimulation phase from the internally calculated fixed voltage $V_{REFStim}$, for comparison following the end of the balance phase of pulse P and before the beginning of the next stimulation phase.

Figure 9:
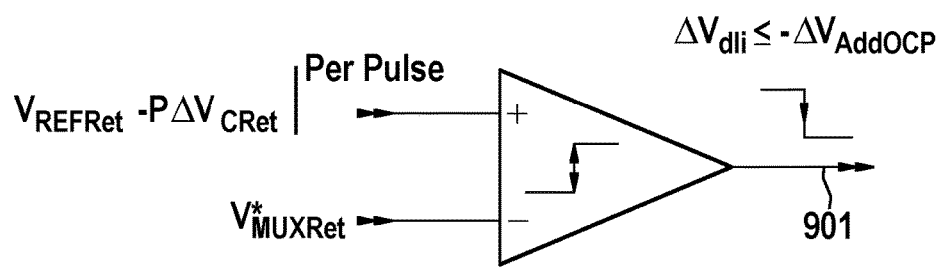
Figure 9:
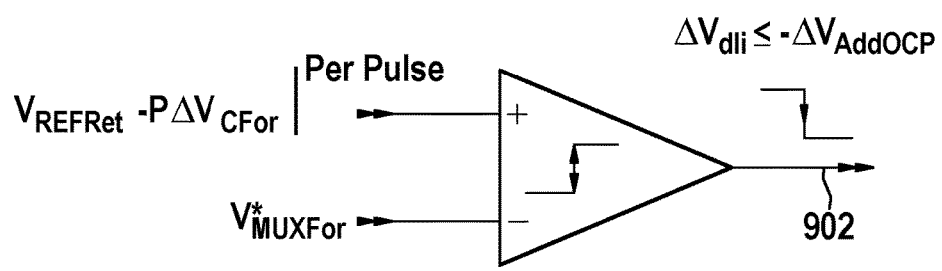

Similarly, conditions (19.b) and (19.c) are implemented by the comparators of FIG. 9, where a third and fourth internal DAC generate the variable comparison voltages.

If a comparator of FIG. 8 or FIG. 9 triggers (i.e., if outputs 801, 901, or 902 change logic value), after P pulses (a counter is kept in the IPG 700), the corresponding double-layer capacitance and blocking capacitor of the monitored electrode will be discharged.

Figure 10:
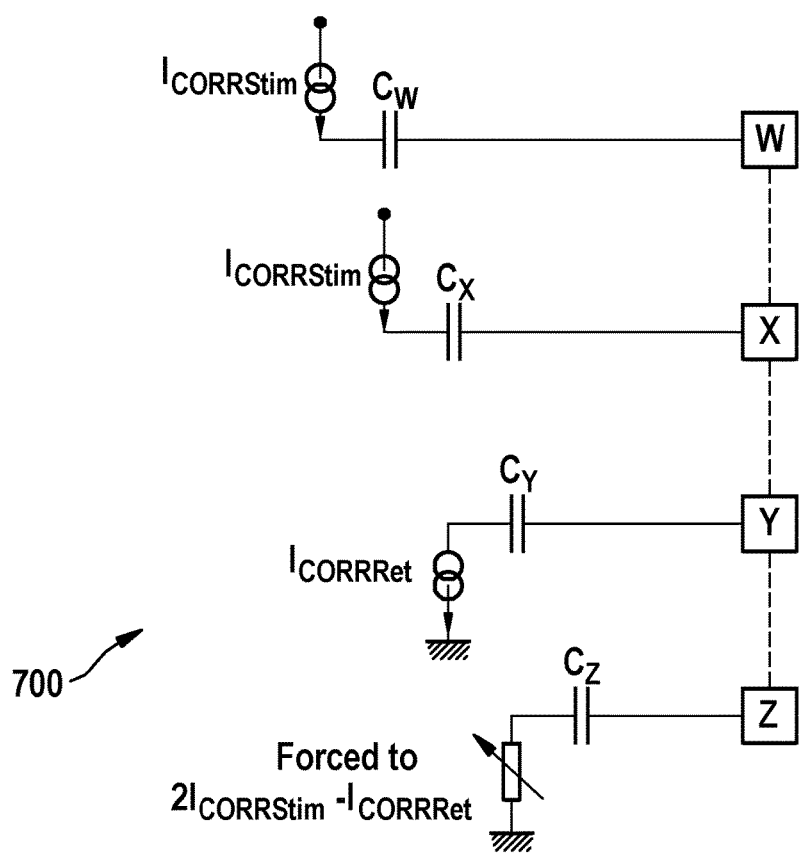
FIG. 10 shows a correction phase for cancelling accumulated double layer voltages.

To do so, in a preferred version, a correction phase is implemented, with an example being shown in FIG. 10. A single correction current $I_{CORR}$ will be forced to circulate, which will result in real currents $I_{CORRStim}$ for the stimulating electrodes (W and X in the example) and $I_{CORRRet}$ for the return electrodes (only Y in the example). The forced electrode (Z in the example) will handle the difference between the correcting currents.

Figure 11:
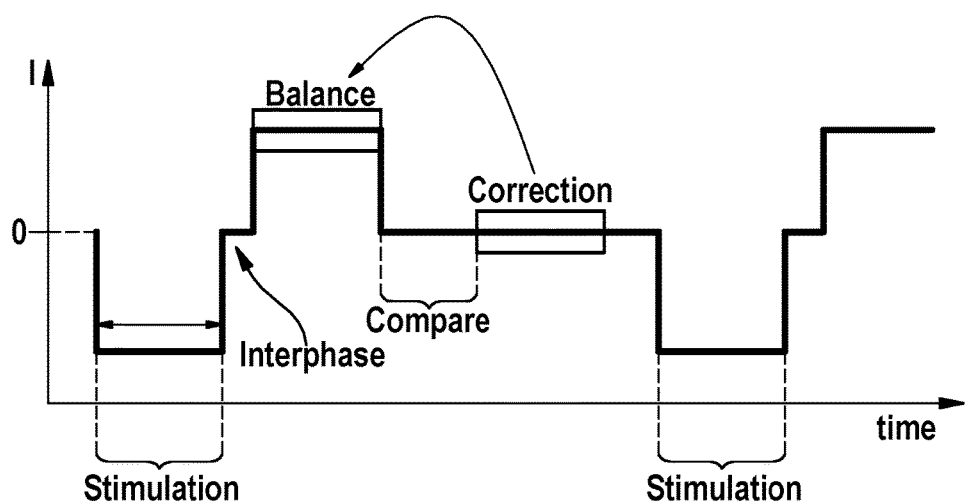
FIG. 11 shows a compare phase preceding a correction phase.

Such correction phases particularly take place following the compare phases (where conditions 18 are evaluated) as shown in FIG. 11. It is also possible to stagger the compare and correction phases so they occur in subsequent pulses. In an alternative version, the correction phase is part of the balance phase (e.g., as shown) where the currents of the balance phase are adjusted accordingly, so as to reduce or cancel the respective accumulated double layer voltage.

In a preferred version, current $I_{CORR}$ is programmed equal to two times $I_{minDiff}$.

Since it is unknown which capacitor has accumulated more charge, $C_{Output}$ or $C_{dlOutput}$ for the active electrode whose $V^*_{MUXOutput}$ triggered a comparator, the system 1 needs to deliver up to P pulses and stop if $\Delta V_{dlOutput}$ reaches zero voltage ($\Delta V_{COutput}$ will still be positive or negative depending on the electrode). This avoids inverting the charging conditions of the stimulating and return electrodes. Hence, during the injection of the correction phases, the system will make sure the following conditions are satisfied:

$$\Delta V_{dlStim} = V_{REF} + V_{OCP} - \Delta V_{CStim} - V^*_{MUXStim} \geq 0 \quad (20.a)$$

$$\Delta V_{dlRet} = V_{REF} + V_{OCP} - \Delta V_{CRet} - V^*_{MUXRet} \leq 0 \quad (20.b)$$

$$\Delta V_{dlFor} = V_{REF} + V_{OCP} - \Delta V_{CFor} - V^*_{MUXFor} \leq 0 \quad (20.c)$$

or re-written as $$V^*_{MUXStim} \leq V_{REF} + V_{OCP} - \Delta V_{CStim} \quad (21.a)$$

$$V^*_{MUXRet} \geq V_{REF} + V_{OCP} - \Delta V_{CRet} \quad (21.b)$$

$$V^*_{MUXFor} \geq V_{REF} + V_{OCP} - \Delta V_{CFor} \quad (21.c)$$

or re-written as $$V^*_{MUXStim} \leq V_{REFFIG5} - \Delta V_{CStim} \quad (22.a)$$

$$V^*_{MUXRet} \leq V_{REFFIG5} - \Delta V_{CRet} \quad (22.b)$$

$$V^*_{MUXFor} \leq V_{REFFIG5} - \Delta V_{CFor} \quad (22.c)$$

or re-written as $$V^*_{MUXStim} \leq V_{REFFIG5} - (P-R)^* \Delta V_{CStim}|^{Per\ Pulse} \quad (23.a)$$

$$V^*_{MUXStim} \geq V_{REFFIG5} - (P-R)^* \Delta V_{CRet}|^{Per\ Pulse} \quad (23.b)$$

$$V^*_{MUXStim} \leq V_{REFFIG5} - (P-R)^* \Delta V_{CFor}|^{Per\ Pulse} \quad (23.c)$$

Figure 12:
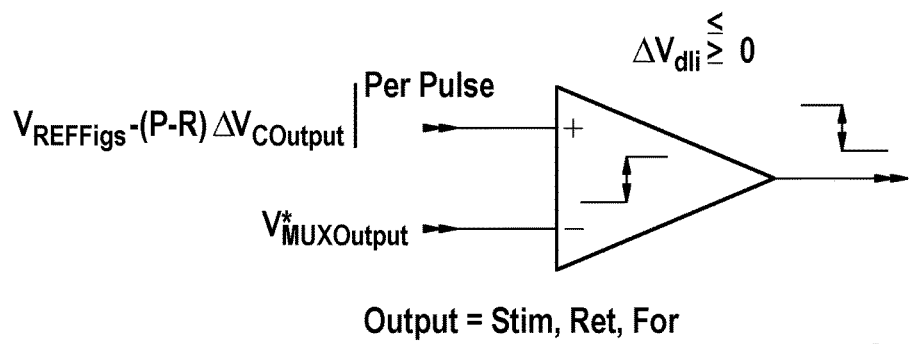
FIG. 12 shows a comparator for stopping the injection of a correction phase.

After R correction phase pulses (R≤P), $R^* \Delta V_{COutput}|^{Per\ Pulse}$ has been subtracted from the accumulated $\Delta V_{COutput}$ (given $I_{CORR}$ equals $2^*I_{MinDiff}$) so $V^*_{MUXOutput}$ (of the triggered comparator) needs to be compared against a variable reference equal to $V_{REFFIG5} - (P-R)^* \Delta V_{COutput}|^{Per\ Pulse}$, as shown in FIG. 12.

If the comparator in FIG. 12 is triggered, or R equals P, the correction phase is stopped and actual electrical stimulation of the target as per FIG. 7 resumed.

In summary, the invention automatically maintains safe electrode and tissue operation without altering the classical IPG 700 front-end, thereby complying with required safety standards. The use of comparators and not measurements during therapeutic electrical stimulation of the target advantageously minimizes overhead consumption for safe operation.

When the system 1 is a spinal cord stimulator (SCS), the invention allows clinical testing of a multiple-electrode pattern at a tonic frequency (e.g., 40 Hz) that calms pain with associated paresthesia, running a determination stage, and increasing the stimulation frequency to the kHz range to avoid paresthesia. In contrast, conventional SCS products are limited to two electrodes at the kHz range.

In an alternative version of the invention, a finer automatic determination of the balance phase permits evoked response sensing for closed-loop neurostimulation, and without the need for post-balance phase compensation to minimize the stimulus artifact (SA). In this alternative version, if $\Delta V_{dli}$ is positive and within $\Delta V_{biph}$ (e.g., 5 mV) during the stimulation phase, the balance phase for the cycled electrode "i" can be left as programmed for the determination stage. No adjustments are necessary as the positive voltage indicates that the mismatch in the real $I_{Ni}$ and real $I_{Pi}$ is causing the balancing charge to be less than the stimulation charge, and the remnant voltage can be handled by the evoked compound action potential (ECAP) recording front-end. The parameter $\Delta V_{biph}$ is preferably programmable.

If $\Delta V_{dli}$ is positive but larger than $\Delta V_{biph}$, the balancing phase current $I_{Pi}$ needs to be increased for better charge compensation. The required increase can be estimated as follows:

A prior impedance measurement allows determination of $C_{dli}$ (with a certain error) for the electrode "i" under consideration (either W or X in the example). Thus, the current $I_{Morei}$ required to be added to the automatically selected $I_{Pi}$ in this case is estimated as $$I_{Morei} = [C_{dli} * (\Delta V_{dli} - \Delta V_{biph1/2})]/(MPW)(i=W\ or\ X) \quad (24)$$

where $\Delta V_{biph1/2}$ is the mid-range point of $\Delta V_{biph}$, and PW is the programmed pulse width as defined above.

A lookup table can be implemented in the IPG 700 to determine each $I_{Morei}$ based on the corresponding $C_{dli}$, $(\Delta V_{dli} - \Delta V_{biph1/2})$ and (M PW).

On the other hand, if $\Delta V_{dli}$ is negative, this implies the electrode potential moved positively pulse after pulse during the M pulses, and thus less balancing charge is required per pulse to avoid this situation. The required reduction may be estimated as follows:

$$I_{Lessi} = [C_{dli} * (-\Delta V_{dli} + \Delta V_{biph1/2})]/(MPW)\ (i=W\ or\ X\ in\ the\ example) \quad (25)$$

The same lookup table for $I_{Morei}$ can be used for determining $I_{Lessi}$.

$I_{Pi}$ will then be re-programmed equal to $$new\ I_{Pi} = old\ I_{Pi} \pm (I_{Morei}\ or\ I_{Lessi})\ (i=W\ or\ X\ in\ the\ example) \quad (26)$$

After initially cycling through all stimulating electrodes, a new set of M pulses, with the modified balance phase, is injected for the stimulating electrodes that required $I_{Pi}$ adjustment. A new $I_{Diffi}$ then estimated and stored, confirming $\Delta V_{dli}$ is positive and within $\Delta V_{biph}$.

A similar procedure, as detailed above for the determination stage, is followed for the return electrodes and a forced electrode.

Figure 13:
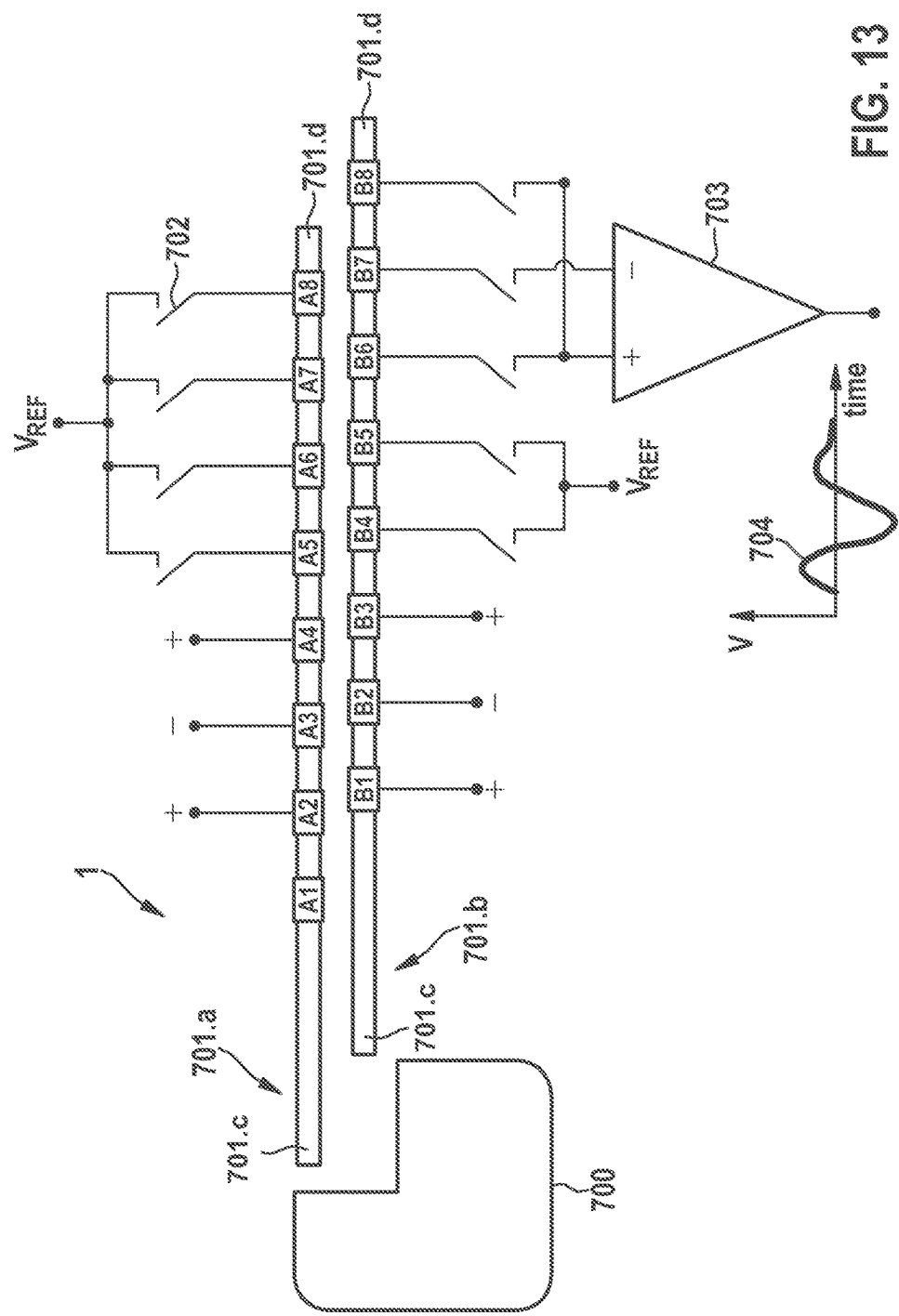
FIG. 13 shows an exemplary version of the invention having a pulse generator (e.g., an implantable pulse generator) and dual percutaneous leads, with three recording electrodes in a quasi-tripolar configuration.

Once the balance phase is automatically determined for the desired stimulation, in a version of the invention adapted for evoked response sensing, a quasi-tripolar arrangement of electrodes with a body drive is utilized for evoked compound action potential (ECAP) recording. FIG. 13 shows the system 1 of FIG. 2 in the form of an implantable SCS system including an IPG 700 and dual percutaneous leads 701.a and 701.b, each extending from a proximal end 701.c to a distal end 701.d. A typical guarded cathode configuration for stimulation is shown, i.e., A3 and B2 are stimulating electrodes which are surrounded by return electrodes A2, B1, A4 and B3. (This is merely an exemplary arrangement, and other electrodes could be chosen as stimulating and return electrodes.) These electrodes may have differently-valued sourcing and sinking currents to steer the electrical field as desired.

Following a programmable blanking period following stimulus delivery, intermediate unused electrodes A5, A6, A7 and A8 and B4, B5 are connected to a voltage reference $V_{REF}$ (internally generated by the IPG 700) via switches 702 which "drive" the body common mode for recording. Blanking may be accomplished via disconnection of switches 702 and/or by other methods of placing the ECAP recording front-end 703 in a state so as to minimize the artifactual effect of the blanking termination.

The end electrodes B6 and B8 are tied together and connected to the non-inverting input of the ECAP recording front-end 703, whereas the center electrode B7 is connected to the inverting input. The ECAP recording electrodes are preferably selected as far away as possible from the stimulating electrodes to minimize the stimulus artifact (SA). Alternatively, recording can occur using A6 tied to A8 as an electrode and A7 as the other electrode, and A5 and B4, B5, B6, B7, and B8 connected to $V_{REF}$.

The recording front-end 703 preferably has a programmable input range and band-pass characteristic, adjustable gain, high input impedance, low equivalent input noise level and power consumption, adequate settling time, high power supply rejection ratio (PSRR), and high common mode rejection ratio (CMRR), among other features.

High CMRR allows rejection of electromyographic (EMG) signals of nearby muscles, as explained below. FIG.

14 shows a first-order impedance model considering the use of B6, B7, and B8 as recording electrodes.

Elements $Z_{B6}$, $Z_{B7}$, and $Z_{B8}$ model the impedance that exists between each electrode and the fiber bundle 800. Resistive elements $R_t$ model the resistance of the fiber bundle 800 where the ECAP 704 (see FIG. 13) is travelling, and elements $R_S$ model the shunting presented by the cerebrospinal fluid in the vicinity of the electrodes B6, B7, and B8. Assume an interfering voltage 801 (e.g. EMG and ECG) generates different voltages $V_A$ and $V_B$ in the vicinity of recording electrodes B6 and B8. This would create a voltage $(V_A+V_B)/2$ at electrode B7 given the voltage divider created by Rt//Rs, and assuming the recording front-end 703 presents high impedance (i.e., no current circulates through $Z_{B7}$). Given the small distance between B6 and B8, and negligible differences between them (same area and metal), it can be expected $Z_{B6}$ will be similar to $Z_{B8}$. Hence, given they are shunted together, the non-inverting terminal of the recording front-end 703 will also see voltage $(V_A+V_B)/2$. In this way, the interfering signal 801 appears as a common mode voltage variation for the ECAP recording front-end 703, which can be suppressed with the appropriate high CMRR.

The recorded ECAP 704 has a triphasic shape as shown in FIG. 13 since the quasi-tripolar configuration resolves the second derivative of the ECAP 704 with respect to time.

Figure 14:
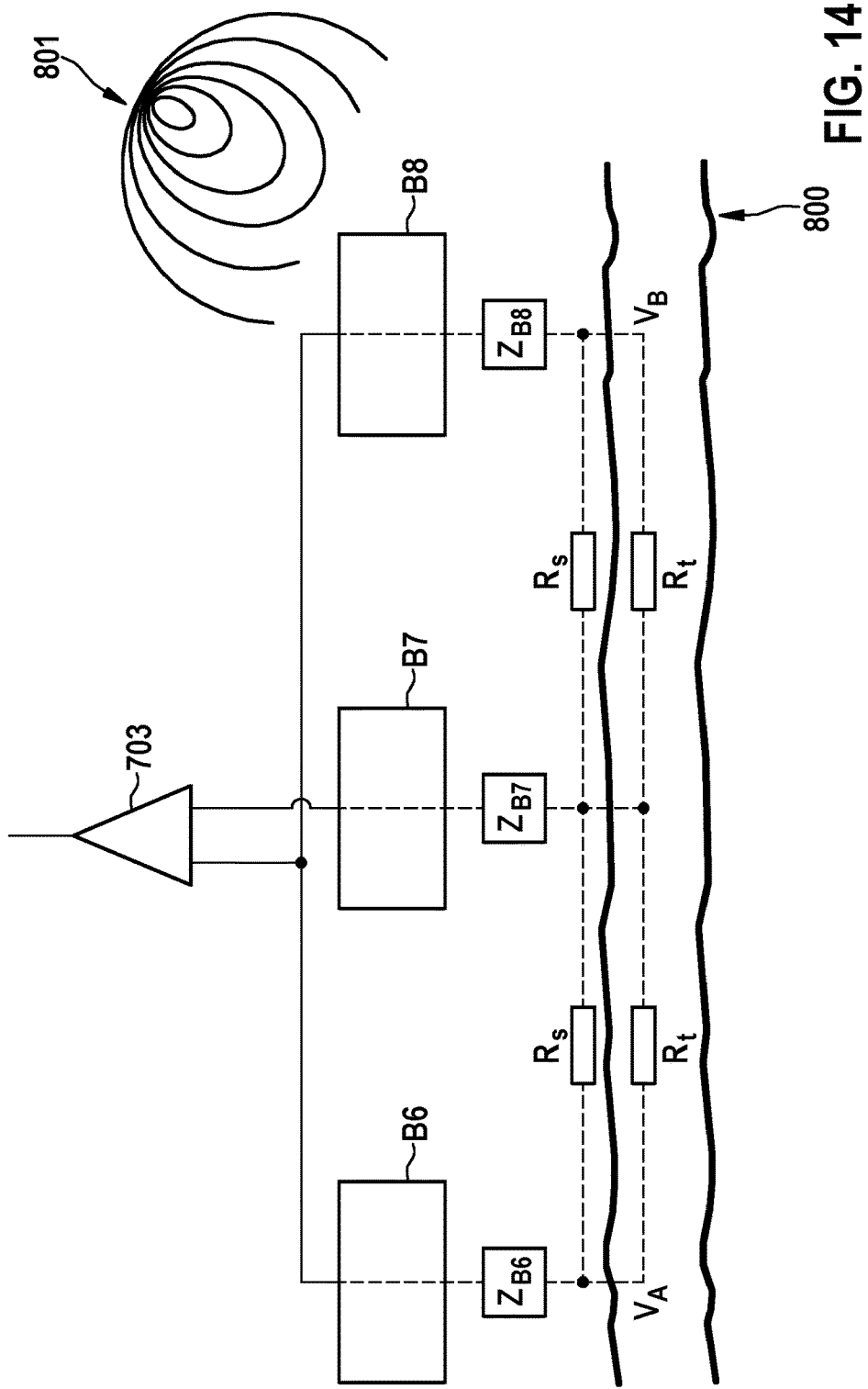
FIG. 14 shows a first order impedance model for three recording electrodes for recording ECAPs.
Figure 15:
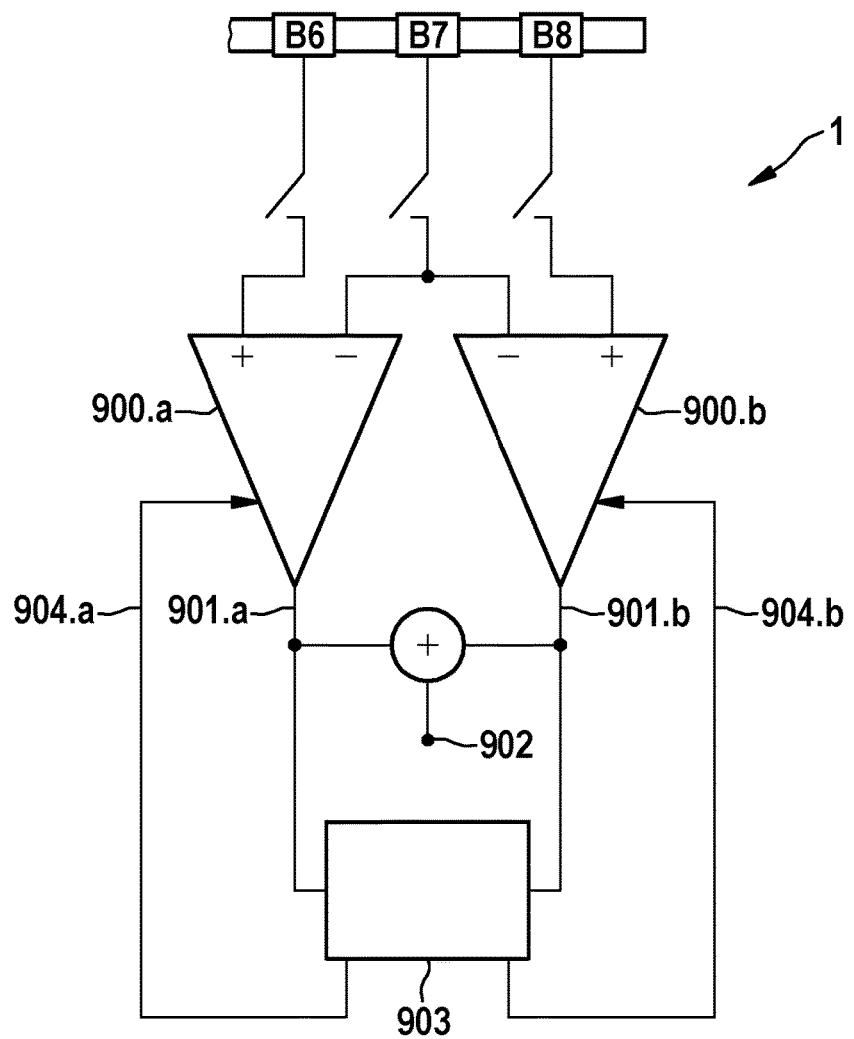
FIG. 15 shows a true tripolar configuration of recording electrodes.

In an alternative arrangement exemplified by FIG. 15, a true tripolar recording configuration is used. Two recording front-ends 900.*a* and 900.*b* are employed, with electrodes B6, B7, and B8 being recording electrodes, with their outputs 901.*a* and 901.*b* being summed to create output 902. Block 903 may be included to compensate for misbalances in the recording impedances (see FIG. 14) to minimize pickup of potentially interfering signals (e.g. EMG, ECG). Block 903 preferably adjusts the gains of 900.*a* and 900.*b*, via control signals 904.*a* and 904.*b* respectively, by minimizing the energy of the difference between outputs 901.*a* and 901.*b*.

As an additional or alternative arrangement, the ECAP recording front-end 703 may be switched to a bipolar recording configuration with body drive after a short period (e.g., several ms) following stimulation to observe non-propagating late responses. This late response may allow identifying whether unwanted activation of the nociceptive reflex arc, or muscle afferents in the dorsal roots, is caused by the programmed therapy.

As another possible feature, adaptive sampling frequencies may be utilized to record ECAPs and late responses.

As yet another possible feature, signal processing of ECAPs may utilize a morphological filter algorithm, given the reduced signal-to-noise ratio. U.S. Pat. No. 8,419,645 B2 describes how morphological operators can be utilized to determine respiration parameters from a transthoracic impedance signal. These operators can be applied in an analogous manner to process ECAPs 704. Additionally or alternatively, ECAPs signal processing may be based on discrete wavelet transforms.

As yet another possible feature, the IPG 700 of the present invention senses ECG signals via electrodes on leads 701.*a*, 701.*b*, or via electrode(s) and the IPG case 201. Upon detection of an R-wave from such ECG signals, and following a programmable delay (e.g. 300-500 ms), ECAP recording may take place in the refractory period of the cardiac cycle to further reduce pickup of heart activity.

As yet another possible feature, ECAP recording may be initiated in combination with a patient posture change automatically detected by circuitry in the IPG 700; and/or with a detected electrode-tissue impedance change; and/or may be manually initiated, or initiated in response to patient-triggered adjustments via a remote control.

Figure 16:
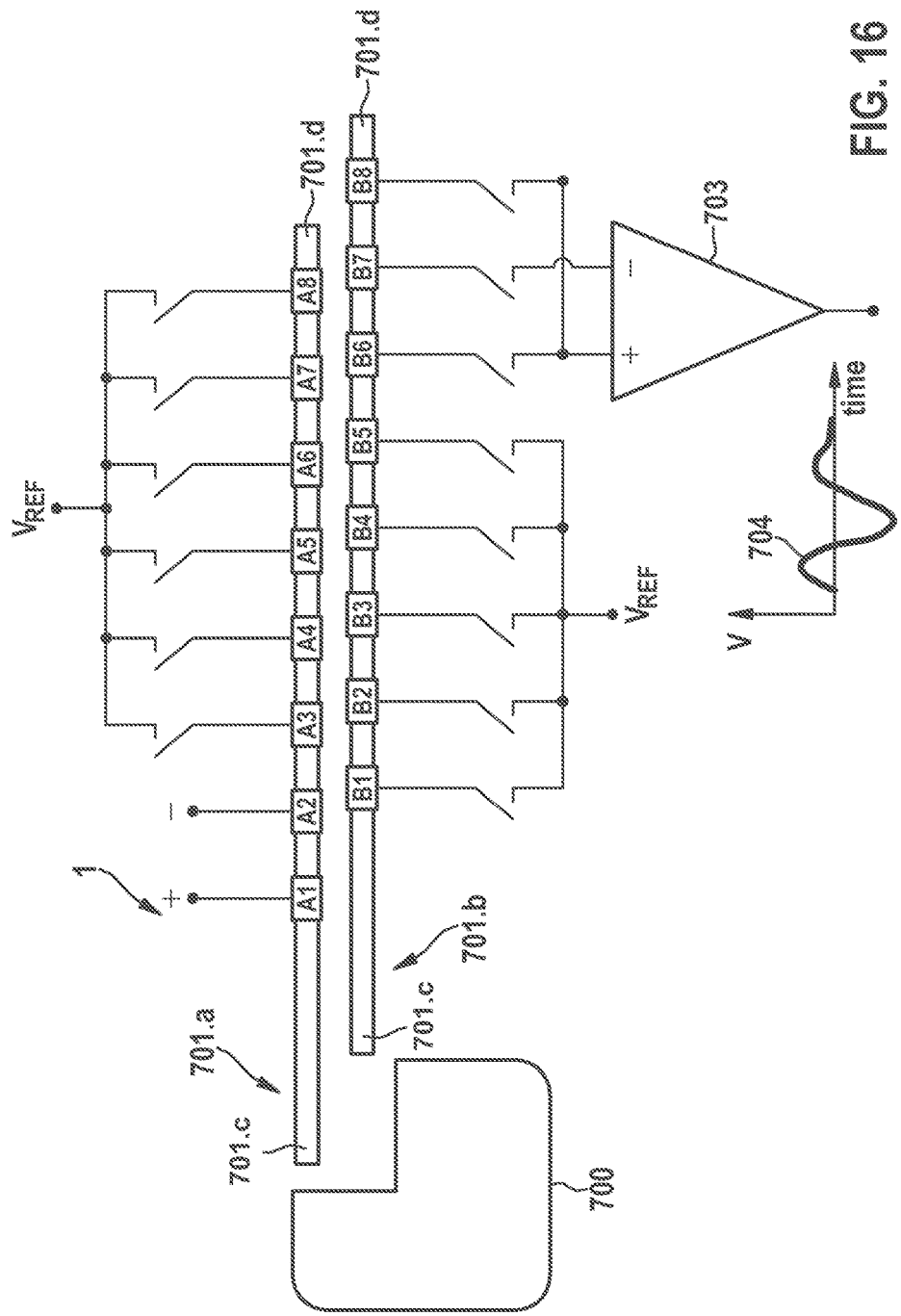
FIG. 16 shows an arrangement for detecting migration of the leads.

As yet another possible feature, the system 1 may provide automatic determination of the relative positions of inter-lead electrodes based on post-stimulus latency value changes of ECAPs 704. Since the IPG 700 controls both the timing of the stimulation pulse delivery and the sampling of ECAPs 704, it can stimulate at one end of lead 701.*a* and record at the other end of lead 701.*b*, thus maximizing the distance between stimulating and recording electrodes, as shown in FIG. 16 for a quasi-tripolar recording configuration. The same arrangement can be used with the true tripolar case shown in FIG. 15.

Preferably, a suitable threshold is defined in an initial ECAP signature, and the latency to this threshold is calculated. This latency value directly corresponds to the physical distance between the stimulating and recording electrode sites following implantation, and is stored in the IPG 700 for future comparisons.

During normal operation, the IPG 700 will occasionally initiate an ECAP 704 as described above. To determine the new ECAP 704 latency, the output of the ECAP recording front-end 703 is compared against the threshold defined using the initial ECAP. Since no subsequent ECAP measurements are required following the initial one, the power and memory required for the purpose of determining relative lead migration is minimized.

If the initial and subsequent latency values are within some acceptable deviation, then it can be assumed leads 701.*a* and 701.*b* have not migrated relative to each other, or that they have migrated an acceptably small amount. An unacceptable deviation may, for example, be defined as an abrupt or significant short-term change from the initial latency value. It can be assumed latency changes due to factors that affect nerve conduction velocity (e.g., drugs) change relatively slowly, whereas relative migration is more likely to cause an abrupt change in latency values. Accordingly, latency comparisons may include non-trended calculations (where the initial value does not change over time) as well as trended calculations (where the initial latency value is adjusted so as to account for slow-varying nerve conduction velocity changes).

A possible arrangement is to deliver a train of stimulation pulses following implantation, and average the corresponding initial ECAPs 704. In some applications, this may be required to improve the signal-to-noise ratio. A threshold for latency determination may be is defined from the averaged initial ECAP 704 signature, and an initial latency calculated. During normal operation, the IPG 700 will occasionally initiate a train of ECAPs 704 as described above. To determine the new ECAP 704 latency, all outputs of the ECAP recording front-end 703 may be averaged and compared against the threshold defined using the initial averaged ECAPs 704.

Upon detection of an unacceptable latency deviation, the IPG 700 can dynamically alter the electrical stimulation of the target (e.g., the electrodes or current steering settings) until the effectiveness of the modified therapy is confirmed (e.g., by ECAPs 704 and/or by the patient). Additionally or alternatively, the IPG 700 might notify a physician of the migration via a remote reporting feature so that corrective action might be taken.

The timing resolution required for detecting lead migration based on ECAP 704 latency changes can be estimated as follows. A large percentage of SCS patients implanted with dual parallel leads experience a mean relative micro-migration of approximately 2-3 mm of stagger between their leads, equivalent to one typical SCS electrode offset (cf. Heller "Lead Migration After SCS a 'Universal Problem'", Anesthesiology News, Pain Medicine, vol. 35:5, May 2009). The Aβ fibers recruited by SCS have typical conduction velocities in the range of 30 to 70 m/s. If the target is to detect 0.2 mm relative changes (for example), this implies a resolution better than 3.0 μs. This imposes a demanding requirement for sampling in the IPG 700, as most digitalization of biosignals (and other internal signals for operation, e.g., battery measurements) is usually done with 10 bits of resolution at a maximum sampling frequency of 100 kS/s.

Figure 17:
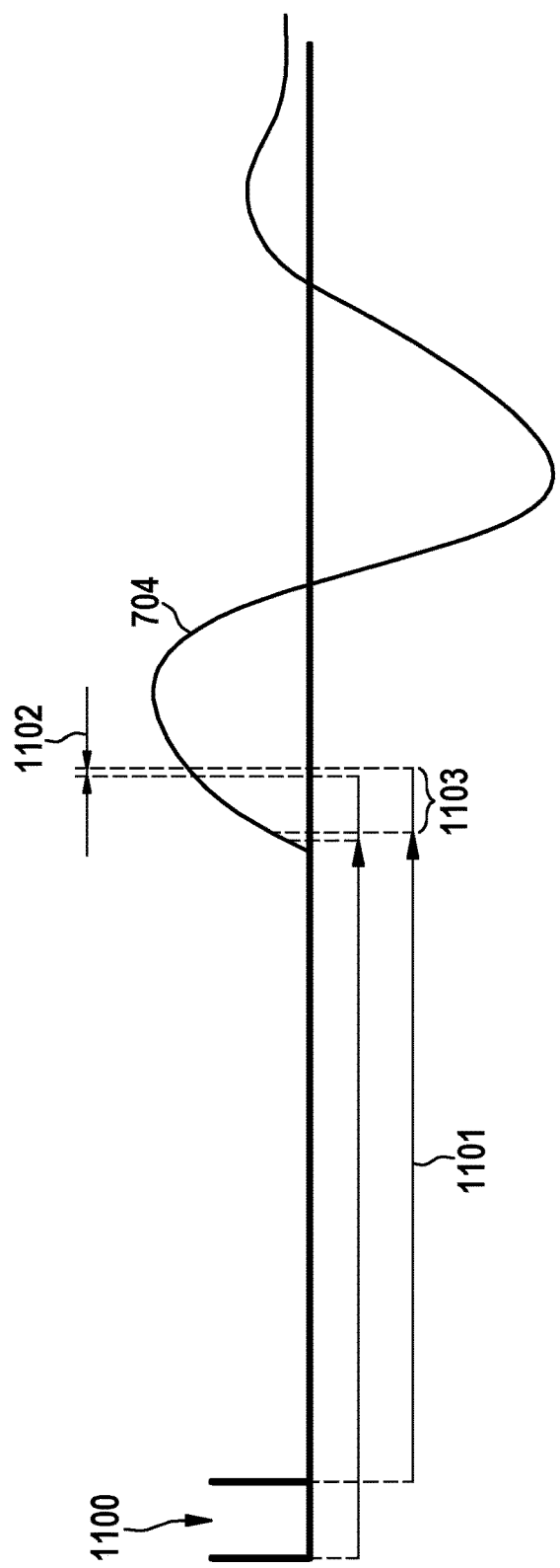
FIG. 17 illustrates principles for determining lead migration using latency of ECAPs.

In a preferred arrangement, as shown in FIG. 17, a train of stimulation pulses 1100 is delivered following implantation, and each initial ECAP 704 for each pulse is sampled with a stimulus-to-start-of-sample timing 1101, or blanking-to-start-of sample timing, incremented by a small delta 1102 (less than the sample period). This equivalent-time-sampling (ETS) technique can then be applied to reconstruct the initial ECAP 704 signature with a high degree of temporal accuracy utilizing a reduced sampling frequency (period 1103). As an example, if twenty pulses are used to reconstruct the ECAP 704 and delta 1102 is selected equal to 2.0 μs, this requires a sampling frequency in the order of 25 kHz (a period 1103 of 40 μs), which is below the typical time-base of 32,768 Hz typically used in IPGs 700. ETS can be applied since ECAPs 704 can be considered a repetitive signal in the time period required to deliver the ECAP-generating stimulation train 1100. As in arrangements discussed above, a threshold for latency determination is defined from the reconstructed initial ECAP signature 704, and an initial latency is calculated.

During normal operation, the IPG 700 will occasionally initiate a train of ECAPs 704 as described above. Using the ECAPs 704 generated by the train, a high-resolution ECAP 704 is reconstructed using ETS. To estimate the new latency between stimulating and recording sites, the time where the reconstructed ECAP 704 crosses the selected threshold is determined.

As in arrangements discussed above, if the initial and subsequent latency values are within some acceptable deviation, then it can be assumed leads 701.a and 701.b have not migrated relative to each other, or that they have migrated an acceptably small amount. Latency comparisons may use non-trended calculations, where the initial value does not change over time, and trended calculations, where the initial latency value is adjusted so as to account for slow-varying nerve conduction velocity changes.

Also as in previous arrangements, upon detection of an unacceptable deviation, the IPG 700 can dynamically alter the therapy (e.g., the electrodes or current steering settings) until the effectiveness of the modified therapy is confirmed (e.g., by ECAPs 704 and/or the patient. Additionally or alternatively, the IPG 700 can notify the physician of the migration, via a remote reporting feature, for further corrective action.

In summary, the foregoing arrangements for ECAPs recording advantageously provide a balance phase for a given stimulation phase in a multi-electrode system that returns the electrodes within mV of their open circuit potentials (OCPs), thereby terminating Faradaic reactions caused by stimulation, and thus minimizing the stimulus artifact (SA) for evoked compound action potential (ECAP) recording. The invention further provides recording configurations for ECAPs, particularly in spinal cord stimulation (SCS) devices, that minimize the pick-up of interfering signals such as remnant SA, electromyographic (EMG) activity caused by nearby muscles, and heart activity (ECG).

Finally, the invention further provides a robust method for determining relative lead migration, particularly in neurostimulation systems with several implanted leads. The method can deliver high temporal resolution utilizing a reduced sampling rate.

Exemplary versions of the invention have been described above in order to illustrate how to make and use the invention. The invention is not intended to be limited to these versions, but rather is intended to be limited only by the claims set out below. Thus, the invention encompasses all different versions that fall literally or equivalently within the scope of these claims.

What is claimed is:

1. A method for automatic charge balancing during delivery of electrical stimulation to tissue using a pulse generator (700), the pulse generator (700) having:
   I. a stimulating electrode (W, X),
   II. a return electrode (Y), and
   III. a forced return electrode (Z),
   wherein:
   A. the stimulating electrode (W, X), the return electrode (Y), and the forced return electrode (Z) are configured to deliver the electrical stimulation,
   B. each electrode (W, X, Y, Z) is coupled by a respective DC-blocking capacitor ($C_i$) to a current source (S), a current sink (S'), or a voltage, and
   C. each electrode (W, X, Y, Z) defines a capacitance ($C_{dli}$) when forming a double layer with adjacent tissue,
   the method including the steps of:
   a. in a determination stage, programming stimulation current pulses ($I_{Ni}$) and determining balancing current pulses ($I_{Pi}$) for each electrode (i=W, X, Y, Z) wherein:
      (1) for the stimulating electrode (W, X), the difference between the stimulation current pulse ($I_{Ni}$) and balancing current pulse ($I_{Pi}$) is a positive value;
      (2) for each of the return electrode (Y) and the forced return electrode (Z), the difference between the stimulation current pulse ($I_{Ni}$) and the balancing current pulse ($I_{Pi}$) is:
         (a) positive, and
         (b) less than or equal to the difference between the stimulation current pulse ($I_{Ni}$) and balancing current pulse ($I_{Pi}$) for the stimulating electrode (W, X);
   b. in a stimulation stage following the determination stage:
      (1) repeatedly applying stimulation cycles via the stimulating electrode (i=W, X) and the return electrode, each stimulation cycle including:
         (a) the stimulation current pulse ($I_{Ni}$);
         (b) the balancing current pulse ($I_{Pi}$) following the stimulation current pulse ($I_{Ni}$);
         (c) an open circuit phase (OCP) following the balancing current pulse ($I_{Pi}$), wherein no current is applied via the stimulating electrode (W, X);
      (2) monitoring at least one of the electrodes (W, X, Y, Z); and
      (3) generating correction currents ($I_{CORRStim}$, $I_{CORRRet}$) when an accumulated voltage ($\Delta V_{dli}$) at the double layer of any of the monitored electrodes crosses pre-defined thresholds ($-\Delta V_{AddOCP}$, $\Delta V_{SubOCP}$), wherein the correction currents ($I_{CORRStim}$, $I_{CORRRet}$) reduce the accumulated voltage ($\Delta V_{dli}$).

2. The method of claim 1 wherein any crossing of the pre-defined thresholds ($-\Delta V_{AddOCP}$, $\Delta V_{SubOCP}$) by the accumulated voltage ($\Delta V_{dli}$) of one of the monitored electrodes is detected by comparing:

a. a voltage on a terminal of the DC-blocking capacitor C0 opposite the monitored electrode, and
b. the difference between:
  (1) a voltage reference, and
  (2) an estimated accumulated voltage ($P^*\Delta V_{CStim}|^{Per\ Pulse}$, $P^*\Delta V_{CRet}|^{Per\ Pulse}$, or $P^*\Delta V_{CFor}|^{Per\ Pulse}$) at the DC blocking capacitor ($C_i$) of the monitored electrode.

3. The method of claim 2 wherein the stimulation current pulse ($I_{Ni}$) and/or the balancing current pulse ($I_{Pi}$) are determined in dependence on:
  a. patient posture, and/or
  b. stimulation cycle frequency.

4. The method of claim 3 wherein the determination stage includes providing stimulation current pulses ($I_{Ni}$) from each electrode (i=W, X, Y, Z) to a reference electrode (201).

5. The method of claim 4 wherein the reference electrode (201) is defined by a casing (201) of the pulse generator (700).

6. The method of claim 1 wherein the stimulation current pulse ($I_{Ni}$) and/or the balancing current pulse ($I_{Pi}$) are determined such that any stimulus artifact (SA) resulting from a stimulation cycle is minimized.

7. The method of claim 6 further including the step of sensing evoked compound action potentials (ECAPs), each evoked compound action potential resulting from one of the stimulation cycles.

8. The method of claim 7 wherein evoked compound action potentials (ECAPs) are sensed using at least one of:
  a. adaptive frequencies, and/or
  b. equivalent-time sampling techniques.

9. The method of claim 7 wherein evoked compound action potentials (ECAPs) are sensed using three recording electrodes (B6, B7, B8).

10. The method of claim 9 wherein:
  a. the recording electrodes (B6, B7, B8) are provided on at least one implantable lead connected to the pulse generator (700), and
  b. the recording electrodes (B6, B7, B8) are provided in:
    (1) a tripolar arrangement, or
    (2) a quasi-tripolar arrangement.

11. The method of claim 9 wherein:
  a. the pulse generator (700) includes first and second leads (701.a, 701.b);
  b. one of the leads (701.a, 701.b) has the stimulating electrode (A3, B2) and return electrode (A2, A4, B1, B3) thereon, with the stimulating electrode being guarded by the return electrode; and
  c. one of the leads (701.a, 701.b) has the recording electrodes (B6, B7, B8) thereon.

12. The method of claim 11 wherein:
  a. the stimulating electrode (A3, B2) is situated closer to a proximal end of one of the leads than the recording electrodes (B6, B7 B8), and the recording electrodes (B6, B7, B8) are situated closer to a distal end of one of the leads than the stimulating electrode (A1, B2); or
  b. the stimulating electrode (A3, B2) is situated closer to a distal end of one of the leads than the recording electrodes (B6, B7, B8) and the recording electrodes (B6, B7, B8) are situated closer to a proximal end of one of the leads than the stimulating electrode (A3, B2).

13. The method of claim 11 further including the step of detecting changes in relative positioning of the leads (701.a, 701.b), the step including determining latency value changes of ECAPs.

14. The method of claim 1 wherein each electrode (W, X, Y, Z) is coupled to its respective current source (S), current sink (S'), or voltage solely via its respective DC-blocking capacitor (Ci).

15. The method of claim 1 wherein in the determination stage, the stimulation current pulses ($I_{Ni}$) are programmed, and the balancing current pulses ($I_{Pi}$) are determined, such that:
  a. the DC blocking capacitor ($C_i$) and defined capacitance ($C_{dli}$) of each electrode (W, X, Y, Z) charge in the same direction; and
  b. the DC-blocking capacitor ($C_i$) and defined capacitance ($C_{dli}$) of the stimulating electrode (W, X) charge in directions opposite the charging of the DC-blocking capacitor ($C_i$) and defined capacitance ($C_{dli}$) of the return and forced return electrode (Y, Z).

16. A method for automatic charge balancing during delivery of electrical stimulation to tissue using a pulse generator (700), the pulse generator (700) having:
  I. a stimulating electrode (W, X),
  II. a return electrode (Y), and
  III. a forced return electrode (Z),
  wherein:
  A. the stimulating electrode (W, X), the return electrode (Y), and the forced return electrode (Z) are configured to deliver the electrical stimulation,
  B. each electrode (W, X, Y, Z) is coupled by a respective DC-blocking capacitor ($C_i$) to a current source (S), a current sink (S'), or a voltage, and
  C. each electrode (W, X, Y, Z) defines a capacitance ($C_{dli}$) when forming a double layer with adjacent tissue,
  the method including the steps of:
  a. in a determination stage, programming stimulation current pulses ($I_{Ni}$) and determining balancing current pulses ($I_{Pi}$) for each electrode (i=W, X, Y, Z) wherein:
    (1) the DC-blocking capacitor ($C_i$) and defined capacitance ($C_{dli}$) of each electrode (W, X, Y, Z) charge in the same direction;
    (2) the DC-blocking capacitor ($C_i$) and defined capacitance ($C_{dli}$) of the stimulating electrode (W, X) charge in directions opposite the charging of the DC-blocking capacitor ($C_i$) and defined capacitance ($C_{dli}$) of the return and forced return electrode (Y, Z);
  b. in a stimulation stage following the determination stage:
    (1) repeatedly applying stimulation cycles via the stimulating electrode (i=W, X) and the return electrode, each stimulation cycle including:
      (a) the stimulation current pulse ($I_{Ni}$);
      (b) the balancing current pulse ($I_{Pi}$) following the stimulation current pulse ($I_{Ni}$);
      (c) an open circuit phase (OCP) following the balancing current pulse ($I_{Pi}$), wherein no current is applied via the stimulating electrode (W, X);
    (2) monitoring at least one of the electrodes (W, X, Y, Z); and
    (3) generating correction currents ($I_{CORRstim}$, $I_{CORRRet}$) when an accumulated voltage ($\Delta V_{dli}$) at the double layer of any of the monitored electrodes crosses pre-defined thresholds ($-\Delta V_{AddOCP}$, $\Delta V_{SubOCP}$), wherein the correction currents ($I_{CORRStim}$, $I_{CORRRet}$) reduce the accumulated voltage ($\Delta V_{dli}$).

17. The method of claim 16 wherein in the determination stage, the stimulation current pulses ($I_{Ni}$) are programmed, and the balancing current pulses ($I_{Pi}$) are determined, such that for the stimulating electrode (W, X), the difference between the stimulation current pulse ($I_{Ni}$) and balancing current pulse ($I_{Pi}$) is a positive value.

18. The method of claim 16 wherein in the determination stage, the stimulation current pulses ($I_{Ni}$) are programmed, and the balancing current pulses ($I_{Pi}$) are determined, such that for each of the return electrode (Y) and the forced return electrode (Z), the difference between the stimulation current pulse ($I_{Ni}$) and balancing current pulse ($I_{Pi}$) is:
  (1) positive, and
  (2) less than or equal to the difference between the stimulation current pulse ($I_{Ni}$) and balancing current pulse ($I_{Pi}$) for the stimulating electrode (W, X).

* * * * *